US009448246B2

(12) United States Patent
Fox et al.

(10) Patent No.: US 9,448,246 B2
(45) Date of Patent: Sep. 20, 2016

(54) INTEGRATED SEQUENTIAL SAMPLE PREPARATION SYSTEM

(71) Applicant: TRIPATH IMAGING, INC., Burlington, NC (US)

(72) Inventors: William Alan Fox, Burlington, NC (US); Charles L. Carrico, Jr., Burlington, NC (US)

(73) Assignee: TriPath Imaging, Inc., Burlington, NC (US)

( * ) Notice: Subject to any disclaimer, the term of this patent is extended or adjusted under 35 U.S.C. 154(b) by 10 days.

(21) Appl. No.: 14/593,631

(22) Filed: Jan. 9, 2015

(65) Prior Publication Data
US 2015/0132798 A1    May 14, 2015

Related U.S. Application Data

(62) Division of application No. 12/921,965, filed as application No. PCT/US2009/036637 on Mar. 10, 2009, now Pat. No. 8,956,578.

(60) Provisional application No. 61/035,542, filed on Mar. 11, 2008.

(51) Int. Cl.
*G01N 35/00* (2006.01)
*G01N 1/30* (2006.01)
*B04B 11/04* (2006.01)

(52) U.S. Cl.
CPC ............ *G01N 35/0095* (2013.01); *G01N 1/30* (2013.01); *B04B 2011/046* (2013.01); *G01N 2035/00495* (2013.01); *G01N 2035/00504* (2013.01); *Y10T 436/111666* (2015.01)

(58) Field of Classification Search
CPC ............... G01N 35/0095; G01N 2035/00495; B04B 2011/046
See application file for complete search history.

(56) References Cited

U.S. PATENT DOCUMENTS 3,722,790 A    3/1973  Natelson
4,708,940 A    11/1987 Yoshida et al.
(Continued)

FOREIGN PATENT DOCUMENTS

GB    1 326 067 A    8/1973
WO   WO 00/49557 A   8/2000

OTHER PUBLICATIONS

International Preliminary Report on Patentability and Written Opinion for International Application No. PCT/US2009/036637 dated Sep. 14, 2010.
(Continued)

*Primary Examiner* — Jill Warden
*Assistant Examiner* — Julie Tavares
(74) *Attorney, Agent, or Firm* — Lerner, David, Littenberg, Krumholz & Mentlik, LLP

(57) ABSTRACT

The invention provides an integrated sequential sample preparation system using a sequential centrifuge for preparing samples for analysis. Methods of more efficiently preparing discrete samples sequentially for subsequent analysis are also provided. The apparatus and methods for sequentially preparing discrete samples provide improved operating efficiencies over conventional preparation processes that use batch centrifugation systems. Such advantages include reducing dwell time, increasing system throughput, reducing sample preparation system footprint, and improving precision of the analytical process. The integrated sequential preparation system with the integrated sequential centrifuge further provides the capability of handling critical or STAT samples without compromising the operating efficiencies achieved by preparing discrete samples in a sequential manner.

19 Claims, 20 Drawing Sheets

(56) References Cited

U.S. PATENT DOCUMENTS

| | | |
|---|---|---|
| 4,830,832 A | 5/1989 | Arpagaus et al. |
| 5,389,339 A | 2/1995 | Petschek et al. |
| 5,525,240 A | 6/1996 | Lemelson |
| 5,769,775 A | 6/1998 | Quinlan et al. |
| 2002/0132354 A1 | 9/2002 | Downs et al. |
| 2003/0022176 A1 | 1/2003 | Schremp et al. |
| 2006/0051241 A1 | 3/2006 | Higuchi et al. |
| 2006/0073510 A1 | 4/2006 | Fox et al. |

OTHER PUBLICATIONS

International Search Report from International Patent Application No. PCT/US2009/036637, filed Mar. 10, 2009.

INTEGRATED SEQUENTIAL SAMPLE PREPARATION SYSTEM

CROSS-REFERENCE TO RELATED APPLICATIONS

This application is a divisional application of U.S. patent application Ser. No. 12/921,965, which is a national stage application filed under 35 U.S.C. 371 of International Application No. PCT/US2009/036637, filed Mar. 10, 2009, which claims priority from U.S. Provisional Patent Application No. 61/035,542, filed Mar. 11, 2008, each of which is incorporated by reference herein in its entirety

FIELD OF INVENTION

The present invention relates to an automated cytological sample preparation system. In particular, this invention relates to an apparatus for continuously preparing discrete cytological samples for analysis and methods of using the same.

BACKGROUND OF THE INVENTION

Preparation of clinical cytological samples for subsequent analysis requires a sequence of steps that can be exceedingly time consuming if practiced manually. Society's emphasis on improving and economizing health care has created an increased demand on sample analysis to assist with diagnosis and to provide information concerning continuing treatment methodology. These demands require that the sample analysis be accurate and, in many instances, be performed quickly. Indeed, the modern clinical laboratory must be capable of preparing and analyzing samples quickly and accurately to assist with the diagnosis and treatment of a wide range of conditions and diseases.

A sample preparation framework requires various modules in order to process samples before further analysis can be performed. Generally, these modules can include conveyance, sample identification (accessioning) and subsequent tracking, vortexing, sample container preparation, specimen loading into a sample container, centrifugation, removing a centrifuged phase from the sample container, and forming an assay preparation for analysis.

Sample conveyance is the mechanism for transporting a sample between various modules. The means for sample conveyance have conventionally included both manual and automated transport systems. Automated systems can include conveyors or loading arms for facilitating the exchange of samples between processing stations.

Sample identification and tracking is particularly important to ensure custody transfer of cytological samples where the results will lead to a determination of the proper course of medical treatment for a subject. The potential for great physical harm exists if the samples become mixed or the results become improperly reported. Conventionally, samples are typically identified by a sample identifier.

Vortexing ensures the concentrations of components making up the sample are substantially continuous, cell agglomerations that may have formed are substantially broken up, and any entrained gas is substantially removed from the sample. Vortexing is particularly important when there has been a long delay between when the sample was taken and when the sample is prepared for further analysis.

Centrifugation is used to isolate particles in a suspended state from the medium in which they are held. Many research and clinical applications rely on the isolation of cells, subcellular organelles, and macromolecules typically from samples that need to be individually processed. Laboratory and/or clinical centrifugations conventionally are batch processes with most centrifuges designed to process multiple samples at once. When processing multiple, discrete samples, there is a delay in processing earlier samples placed into the centrifuge. This delay is known as dwell time. Furthermore, there must be a sufficient number of samples available to fill the centrifuge or at least there must be enough samples to load the centrifuge in such a way that the centrifuge remains in balance about its rotational axis once centrifugation begins.

Sample container preparation can involve any of a number of activities depending on, among other things, the type of centrifugation being performed and whether used sample tubes are discarded or recirculated.

Conventionally, a variety of means have been used to load a sample into a sample container. Sample loading can be accomplished by a sample transfer system that removes a sample from a container vial and dispenses the sample into a sample container. Sample loading can also include a manual or automated system and/or procedure for placing a sample container holding the sample into a desired position.

The supernatant or sedimentary layers of the centrifuged sample may be removed by a manual or automated system and/or procedure. Centrifuged sample portions may be unloaded by a sample transfer system that removes a sample portion from a sample container and dispenses the sample portion onto an assay device such as a slide or some other sample preparation used for analyzing the sample.

There remains a need in the art to more fully automate the sample preparation process. Eliminating the need for human intervention will allow samples to be processed more quickly; accurately; and, potentially, less expensively. A fully automated system will also reduce the amount of training that is required, reduce the size of the footprint of the automated preparation system, and increase the sample throughput per area of footprint. Further, an automated sample preparation system can reduce the amount of sample that is needed for processing. A fully automated system can also accommodate complete tracking of chain of custody from the sample vial through the final analysis. Further, there remains a need in the art to minimize human intervention reducing the potential that medical or laboratory personnel will come in contact with the specimen, contaminate the sample, or misdirect the sample through human error.

The extent of the idle time of a batch system capable of processing N samples but remaining idle until at least L samples are accumulated, with such samples arriving randomly to the batch system, has been addressed by Mathias A Dümmler and Alexander K. Schömig, "Using Discrete-Time Analysis in the Performance Evaluation of Manufacturing Systems" (paper presented at the annual International Conference on Semiconductor Manufacturing Operational Modeling and Simulation Meeting, San Francisco, Jan. 18-20, 1999). The amount of idle time is dependent upon both the number of samples, if any, remaining in the queue after the $n^{th}$ sequence starts and the number of samples arriving while the $n^{th}$ sequence is underway. The distribution of the number of samples remaining in the queue after the sequence has begun, $y_n(k)$, is given by:

$$y_n(k) = \begin{cases} 0, & k < n-1 \\ \sum_{i=-\infty}^{n-1} \max(0, x_{n-1}(i) - K), & k = n-1 \\ \max(0, x_{n-1}(k) - K), & k > n-1 \end{cases}.$$

while the probability distribution of all prior samples waiting to be processed as they have accumulated at the end of the last sequence, $x_{n-1}$ (k), is represented by:

$$y_n = \max(0, x_{n-1} - K)$$

and $$K = L + \min(\max(0, x_{n-1} - L), N - L).$$

I.e., if the number of samples in the queue to be processed just prior to the $n^{th}$ sequence is greater than the number of samples that can be processed during the sequence, then these samples will wait to be processed in the next sequence. If there are an insufficient number of samples to either fill the batch system or meet the minimum number of samples required by the batch system before a sequence can begin, then there will be idle time in the operation of the batch system until a sufficient additional number of samples become available for processing.

Assuming geometrically distributed arrival times, the distribution of the number of samples arriving during any $n^{th}$ sequence, $\gamma_n(k)$, is given by:

$$\gamma_n(k) = \sum_{m=k}^{\infty} \binom{m}{k} p^k (1-p)^{m-k} b_n(m)$$

where $b_n(m)$ is the distribution along the length of the $n^{th}$ sequence and p is the probability of a sample arriving at any point in time.

The probability distribution of two random variables is given by the convolution theorem. Hence, the probability distribution for the number of samples waiting to be processed after the $n^{th}$ sequence, $x_n(k)$, is given by:

$$x_n(k) = y_n(k) \otimes \gamma_n(k) = \sum_{l=-\infty}^{\infty} y_n(l) \cdot \gamma_n(k-l).$$

I.e., the number of samples waiting to be loaded after the $n^{th}$ sequence for the next $n+1^{th}$ sequence is dependent on the number of samples remaining in the queue to be processed, if any, just prior to starting the $n^{th}$ sequence and the number of samples that have arrived while the $n^{th}$ sequence is underway.

The mean time samples must wait before being processed, $\overline{W}$, is given by Little's law:

$$\overline{W} = \overline{Q}/\overline{R}$$

where $\overline{Q}$ is the mean number of samples in the queue at the start of a sequence given by:

$$\overline{Q} = \Sigma i \cdot x_n(i)$$

and $\overline{R}$ is the average arrival rate of the samples.

Based on Little's formula, the mean waiting time of the samples before being processed, $\overline{W}$, is minimized when there are consistently no samples waiting to be processed at the start of any sequence as long as there are at least a sufficient number of samples, L, available to be processed as required by the batch system.

The study provides revealing mathematical insight, using discrete time analysis, into the problems surrounding the potential limitations on batch processing in discrete time processing systems. As the analysis confirms, where the probability of appearance of a sample is reasonably consistent, then a batch system can be sized such that the idle time resulting from waiting for the requisite number of samples to arrive before a sequence starts can be minimized Indeed, where such probabilities are known, the batch system can be sized such that there are a sufficient number of samples to fill the batch system without any idle time between each sequence and any samples remaining at the end of a given period. However, such consistent probabilities in the clinical setting are rare. There will inevitably be variability in the probability of sample arrivals. Such variability typically is inconsistent and difficult to estimate. Hence, any batch system used in the clinical setting typically needs to be sized for those periods when the probability of arrival of samples is greatest in order to keep up with demand in those peak periods. Inevitably, this will lead to increased idle time when the probability of arrival of a sample is anything less than the maximum probability for which the batch system has been designed.

Conventionally, automated sample preparation systems provide the requisite modules in a subsystem form generally with each module functioning independent of the others within the system. Many of these modules operate in a batch-like manner further complicating the ability to streamline sample processing over the various processing sequences that occur within each of the modules. There remains a need in the art for an automated system that processes discrete cytological specimens wherein each module functions in an integrated manner.

Advancements have been made, for example, in the clinical laboratory to streamline sample processing and reduce the amount of sample that is needed on which to perform an analysis. The need to gain even further efficiency improvements from the sample preparation process has been recognized in the art. For example, U.S. Pat. No. 4,058,252 entitled "Automatic Sample Processing Apparatus" to Williams discloses advancing a number of centrifugation units each having a plurality of containers mounted on a conveyor to various processing stations. U.S. Pat. No. 6,060,022 entitled "Automated Sample Processing System Including Automatic Centrifuge Device" to Pang et al. discloses a centrifugation module that includes loading containers to be processed in a plurality of buckets, checking that the buckets are in balance, loading the buckets into the centrifuge, centrifuging, and unloading the buckets from the centrifuge. However, these systems are limited since the sample holders must be balanced before they are placed in the centrifuge—a process that can prove to be time consuming. Further, these systems are subject to idle time, depending on the availability of samples to be prepared, because the containers or buckets cannot be centrifuged until at least a minimum number of samples have been loaded in such a way that the centrifuge maintains balance. The extent of idle time in these batch processing systems can be determined by the discrete time analysis disclosed herein.

Automated loading and unloading procedures for samples by robotics are disclosed in, for example, U.S. Pat. No. 5,166,889 entitled "Robotic Liquid Sampling System" to Cloyd, U.S. Pat. No. 5,769,775 entitled "Automated Centrifuge for Automatically Receiving and Balancing Samples" to Quinlan, and U.S. Pat. No. 6,374,982 entitled "Robotics for Transporting Containers and Objects within an Automated Analytic Instrument and Service Tool for Servicing Robots" to Cohen et al. However, these automated processing techniques still require that some or all of the preliminary and subsequent sample processing steps be suspended or withheld until centrifugation is complete on the batch of samples being processed in the centrifuge. Furthermore, other modules operating in batch mode—such as the tube handling wheel described in the '889 patent, the weighing station and rack handling robot described in the '775 patent, or the sample handler module described in the '982 patent—can further affect the ability to quickly process samples and streamline the sample preparation operation.

While advancements have been made to streamline processing discrete samples in a cytological sample preparation system, there remains in the art a need to process a varying number of samples in a cytological sample preparation system while reducing, if not eliminating, the idle time of the system resulting from the batch processing of samples in the various modules of the unit.

An additional need that remains in the art is the ability to process irregular critical or emergency samples, otherwise known as STAT samples, that require priority handling without any substantial loss in efficiency of processing other discrete samples in the cytological sample preparation system.

BRIEF SUMMARY OF THE INVENTION

The present invention relates to integrated devices and methods for sequentially preparing discrete samples for further analysis. Without intending to be bound by theory, an integrated sequential sample preparation system and the techniques of the invention provide improved operational efficiencies over conventional preparation systems by reducing dwell time, limiting idle time, requiring smaller sample preparation system footprints, and improving precision of the analytical process.

In one aspect, the invention provides an integrated sequential sample preparation system that includes a sequential centrifuge for centrifuging a sample. The sequential centrifuge has a plurality of sample reservoirs, an indexing system that advances an index from a current available sample reservoir to a next available sample reservoir, a control system that directs the steps of a centrifugation sequence, a sample transfer module for loading a sample into a sample reservoir, and one or more extraction modules for removing a centrifuged sample or portion thereof from the centrifuge.

In an embodiment of the invention, the sample transfer module has an aspiration assembly and a syringing assembly. The sample transfer module may use a syringing pipette system for transferring the sample. The syringing pipette system can include a head assembly that is capable of moving downward in the vertical plane and rotating in the horizontal plane. In an embodiment of the invention, the head assembly of a syringing pipette system has four stations that simultaneously perform different operations. For example, a new syringing pipette is collected at a first station, preferably, from a syringing pipette cartridge that is capable of holding a plurality of syringing pipettes; a sample is extracted from a sample vial and held by the syringing pipette at a second station; the sample is injected, more preferably layered onto a density gradient medium, in a sample container to be centrifuged at a third station; and a used syringing pipette is discarded in the last station.

In certain embodiments of the invention, the syringing pipette comprises a piston assembly having a piston, a piston channel, an annular seal and a piston housing; a cylinder channel; and a tip having a tip opening. The piston channel, defined by the piston housing; piston; and annular seal operate to form a vacuum in the cylinder channel, as the piston is pulled, in order to draw the sample through the tip opening into the cylinder channel.

In another embodiment of the invention, the head assembly of the syringing pipette system moves rotatably in the horizontal plane to at least one of an aliquot preparation station and a diliquot preparation station.

In an embodiment of the invention, the sample transfer module comprises a plurality of syringing pipette assemblies operate substantially simultaneously to dispense at least a portion of each of a plurality of samples into their respective sample reservoirs of the sequential centrifuge.

In certain embodiments of the invention, the extraction module aspirates a supernatant from the centrifuged sample after completing at least one centrifugation sequence. In other embodiments of the invention, a plurality of extractions steps are used over the course of several sequential centrifugation sequences.

The inventive system may also include a centrifuged sample transfer module for removing at least a portion of the centrifuged sample that remains in the sample container, preferably after at least one extraction step, and transfers the removed portion of the centrifuged sample onto an assay device. In a preferred embodiment of the invention, the portion of a centrifuged sample that is removed from the sample container is from substantially one phase, the one phase selected depending upon the type of analysis to be performed. In a prefened embodiment of the invention, the one phase from where the sample is removed is a sedimentary phase. In yet another prefened embodiment of the invention, the amount of time the centrifugation sequence operates is minimized to give only the desired volume of a portion of the centrifuged sample needed to undergo further analysis.

In certain embodiments of the invention, the assay device is a slide, preferably a slide also having disposed on at least a portion of the surface a material that promotes adhesion of the sample to the surface of the slide. In certain prefened embodiments, the inventive system will also include a slide transfer module that advances the slide until the sample becomes substantially adheredly affixed to the slide. In other embodiments, the inventive device may also include a slide preparation module, such as a staining platform, that further prepares the slide for analysis. Preferably, a finished slide will be racked in a slide racking module.

In an embodiment of the invention, the integrated sequential sample preparation system will have a vortexing module to ensure, among other things, the sample is substantially homogenously mixed before being transferred to a sample container. Preferably, the inventive system will also have an accessioning module that assigns a unique identifier to each sample. Other embodiments of the invention may also include at least one sample identification module that identifies the sample. Another embodiment of the inventive preparation system also includes a tracking system for providing chain of custody information for a sample.

In other embodiments of the invention, the sample to be prepared in the inventive system is a critical sample. In yet other embodiments, the inventive system processes and prepares samples having varying levels of priority. In prefened embodiments of the invention, critical or STAT samples will be given special priority for processing in the inventive system.

Another aspect of the invention provides an integrated sample preparation system comprising an accessioning module that assigns a unique identifier to a sample; at least one sample identification module that identifies the sample; a vortexing module to at least one of ensure the components making up the sample are substantially continuous, cell agglomerations that may have formed in the sample are substantially broken up, any entrained gas is substantially removed from the sample, and any combination thereof; a sequential centrifuge that centrifuges the sample; a sample transfer module that loads the sample into a sample reservoir of the sequential centrifuge; at least one extraction module that removes at least a portion of a centrifuged sample; a centrifuged sample transfer module that removes a phase of the centrifuged sample and disposes the phase of the centrifuged sample onto a slide; a slide transfer module that advances the slide until the phase of the centrifuged sample becomes substantially adheredly affixed to the slide; optionally, a slide preparation module that further prepares the slide for analysis; and a slide racking module. According to this aspect of the invention, the accessioning module, the at least one sample identification module, the vortexing module, the transfer assembly, the sequential centrifuge, the at least one extraction assembly, the centrifuged sample transfer module, the slide transfer module, optionally, the slide preparation station, and the slide racking module each are integrated to simultaneously process a plurality of samples.

Another aspect of the invention provides methods for preparing a sample using an integrated sequential sample preparation system. In an embodiment of the invention, the method for preparing a sample in an integrated sequential sample preparation system comprises the steps of accessioning the sample; identifying the sample; vortexing the sample; loading the sample into a current available sample reservoir; centrifuging the sample in a sequential centrifuge; transferring at least a portion of a phase of the centrifuged sample onto an assay device, preferably, a slide; conveying the assay device to a holding module, such as a slide racking module; and loading the assay device in the holding module. In another embodiment of the invention, the conveying step comprises the step of advancing the slide until there is adequate adhesion of the phase of the centrifuged sample to a surface of the slide. In another embodiment of the invention, the assay device is further prepared using a sample preparation module. In yet another embodiment of the invention, the sample preparation module is a staining platform.

In an embodiment of the invention, the accessioning step comprises the step of assigning a unique identifier to the sample. Further to this embodiment, the method for preparing a sample using an integrated sequential sample preparation system additionally comprises the step of identifying the unique identifier of the sample using at least one sample identification module.

In an embodiment of the invention, the loading step comprises the steps of retrieving a syringing pipette, drawing the sample from a sample vial into the syringing pipette, and discarding the syringing pipette. In one embodiment of the invention, at least a portion of the drawn sample may be disposed into the current available sample reservoir by the use of a syringing step. In preferred embodiment of the invention, the loading step further comprises the steps of disposing the sample into the sample vial in order to mix the sample; drawing the mixed sample from the sample vial into the syringing pipette; and syringing at least a portion of the mixed sample into the current available sample reservoir, more preferably, layering the at least a portion of the mixed sample onto a density gradient medium. In yet another preferred embodiment of the invention, the disposing step and the drawing step are repeated at least once before executing the syringing step.

In another embodiment of the invention, the method for preparing a sample using an integrated sample preparation system additionally comprises the step of aspirating a supernatant from the centrifuged sample. Further to this embodiment, the steps of centrifuging the sample and aspirating the supernatant may be repeated at least once.

In an embodiment of the invention, the step for transferring at least a portion of a phase of the centrifuged sample onto an assay device comprises the steps of removing the phase of the centrifuged sample and disposing the phase onto a slide.

In certain embodiments of the invention, the centrifuging step continues for an amount of time needed to give a desired volume of the phase of the centrifuged sample. Preferably, the amount of time is minimized to give only the desired volume of the phase of the centrifuged sample.

In another embodiment of the invention, the sample that is prepared by the method for preparing a sample in an integrated sequential sample preparation system is a critical or STAT sample. Further to this embodiment, the centrifuging step continues until at least one of another critical sample becomes available, a desired total FT has been achieved for the critical sample in the sequential centrifuge, and the desired total FT has been achieved for any other sample in the sequential centrifuge. In another embodiment of the invention, a priority of the another critical sample must be at least the same as or greater than the priority of the critical sample in order to interrupt the centrifuging step.

BRIEF DESCRIPTION OF THE SEVERAL VIEWS OF THE DRAWINGS

Figure 1:
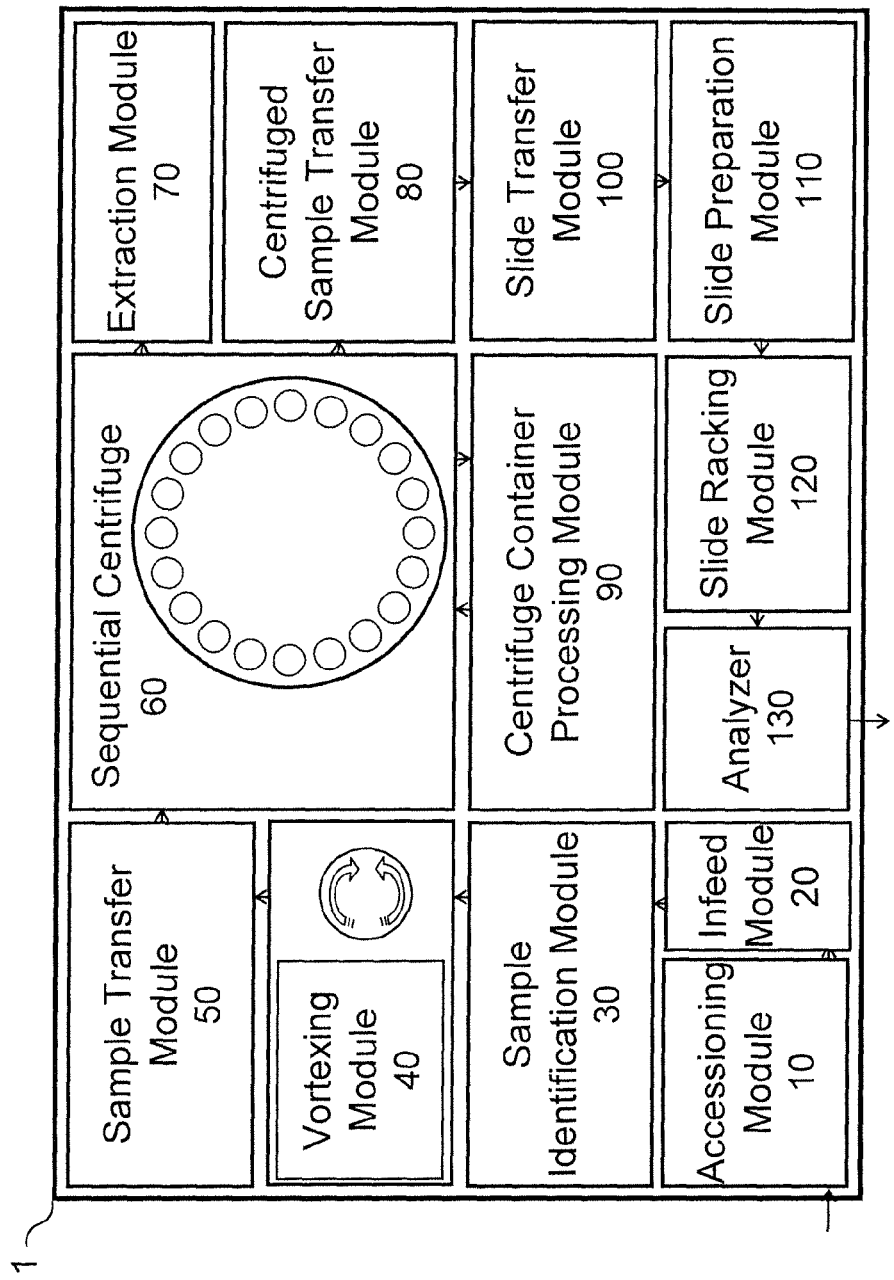
Figure 2:
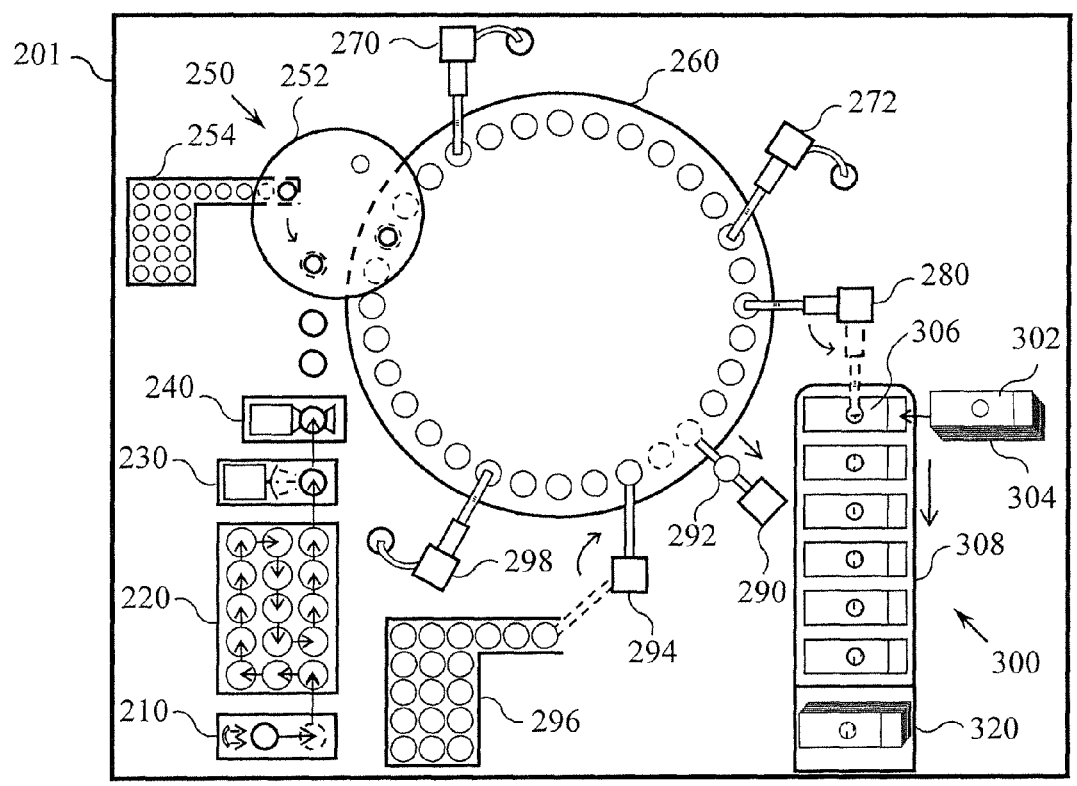
Figure 3:
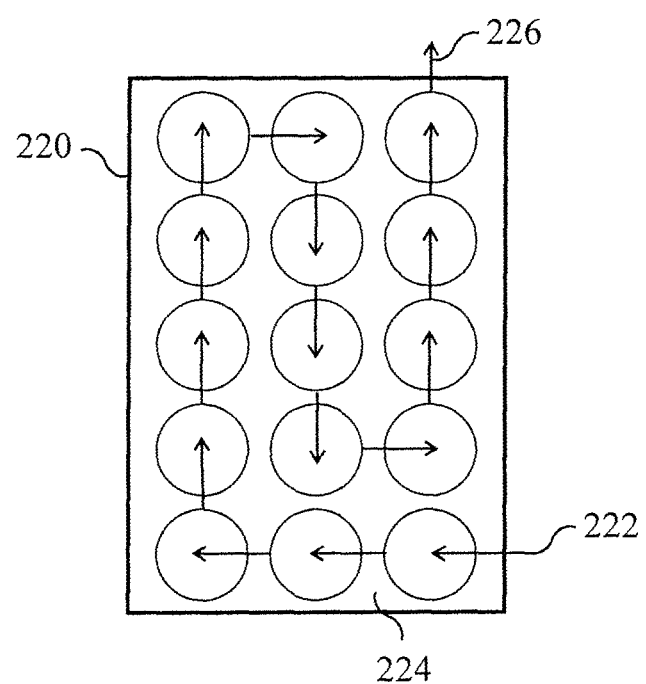
Figure 4:
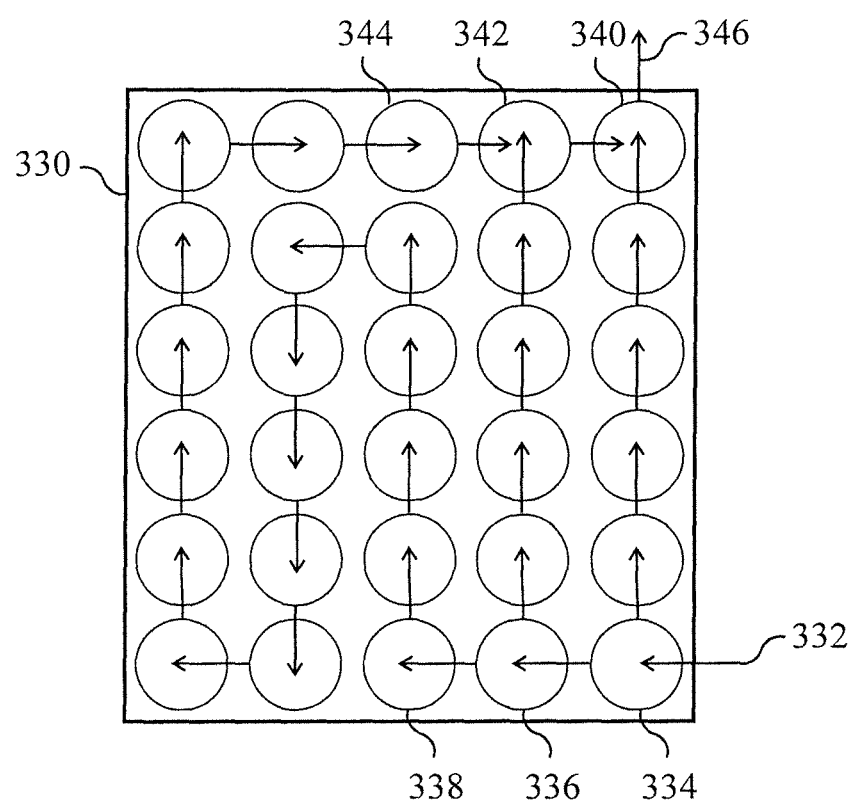
Figure 5:
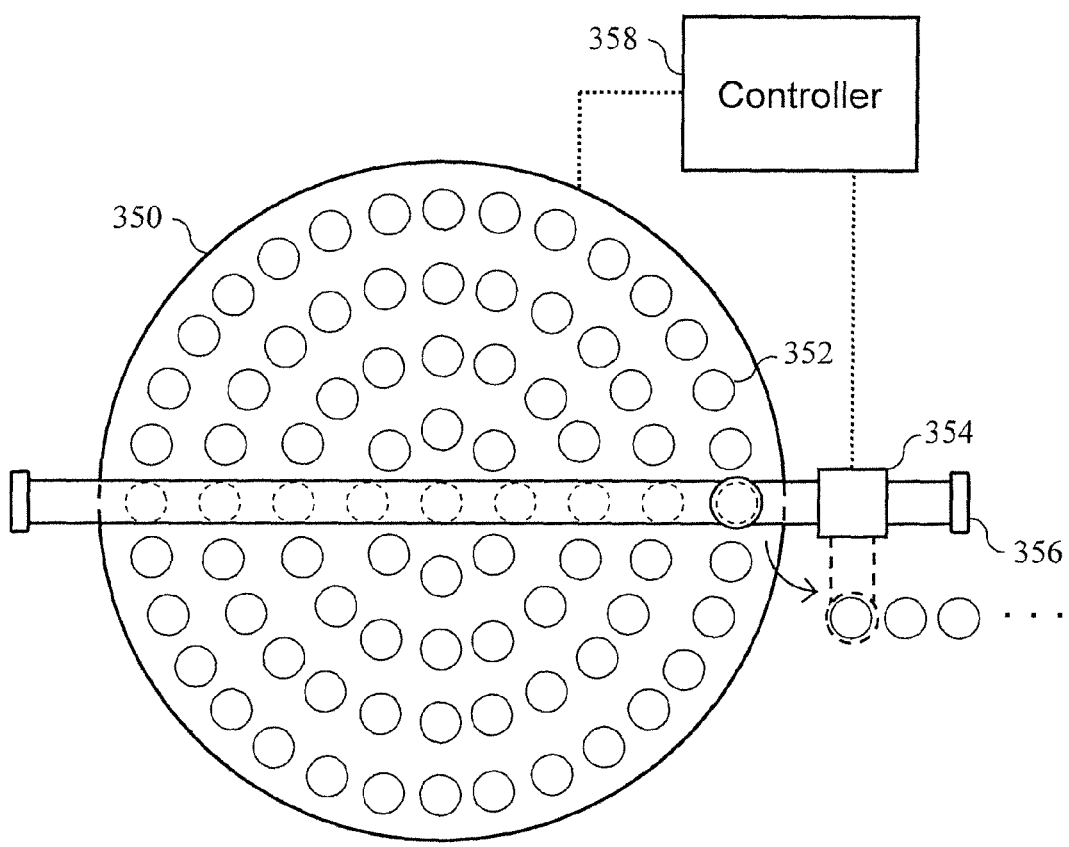
Figure 6:
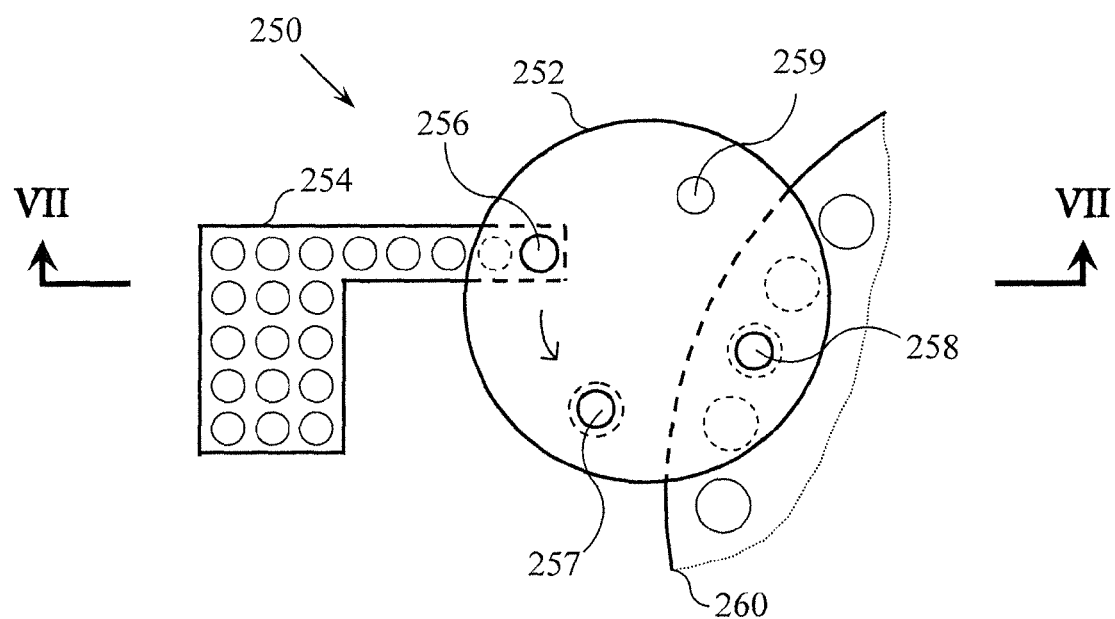
Figure 7:
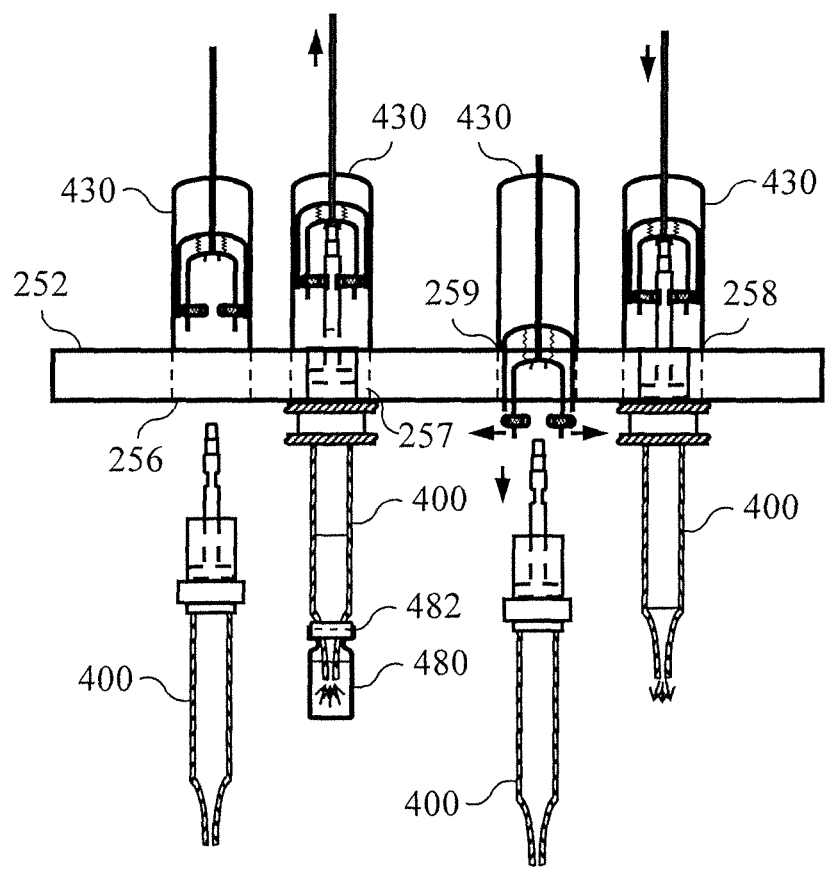
Figure 8:
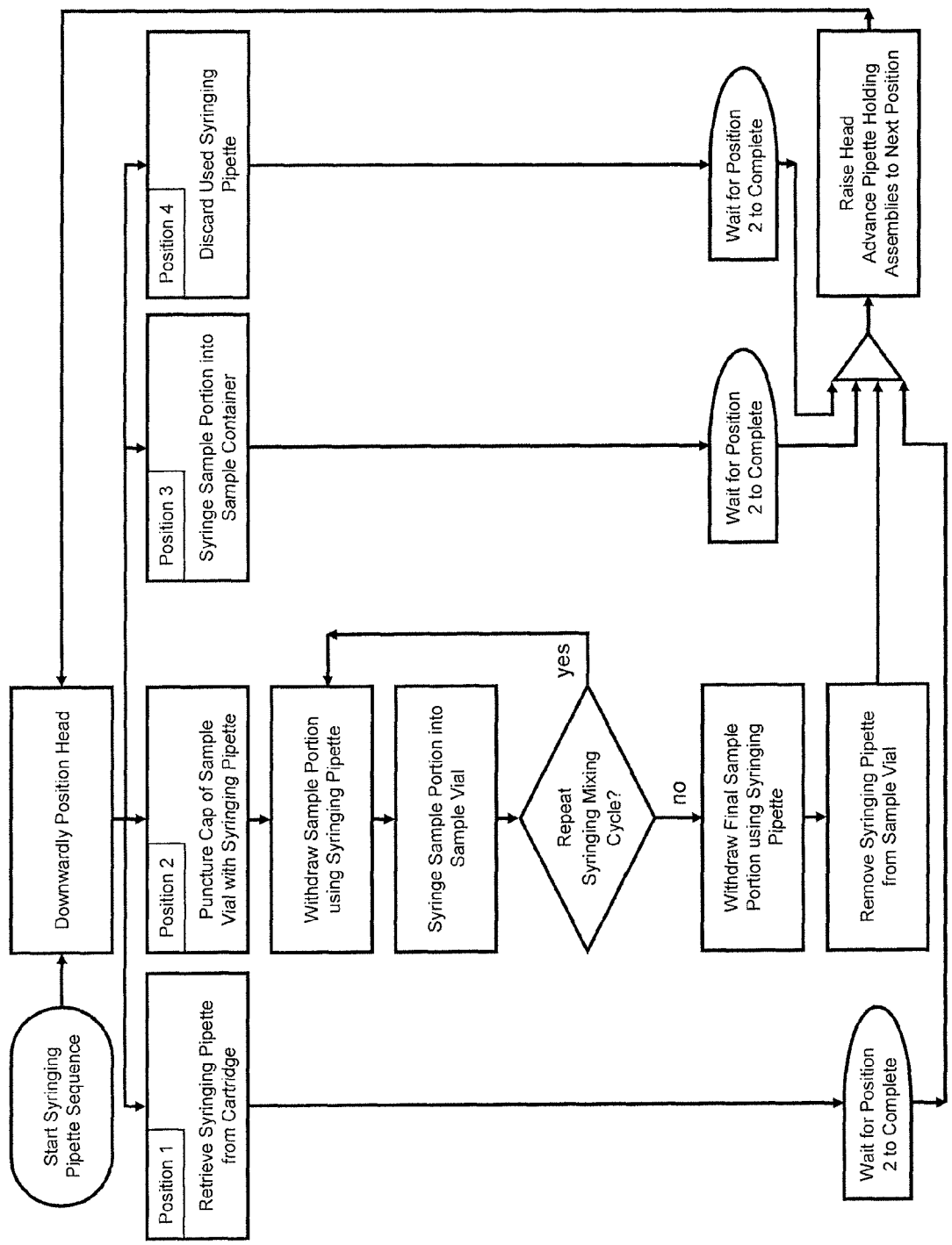
Figure 9:
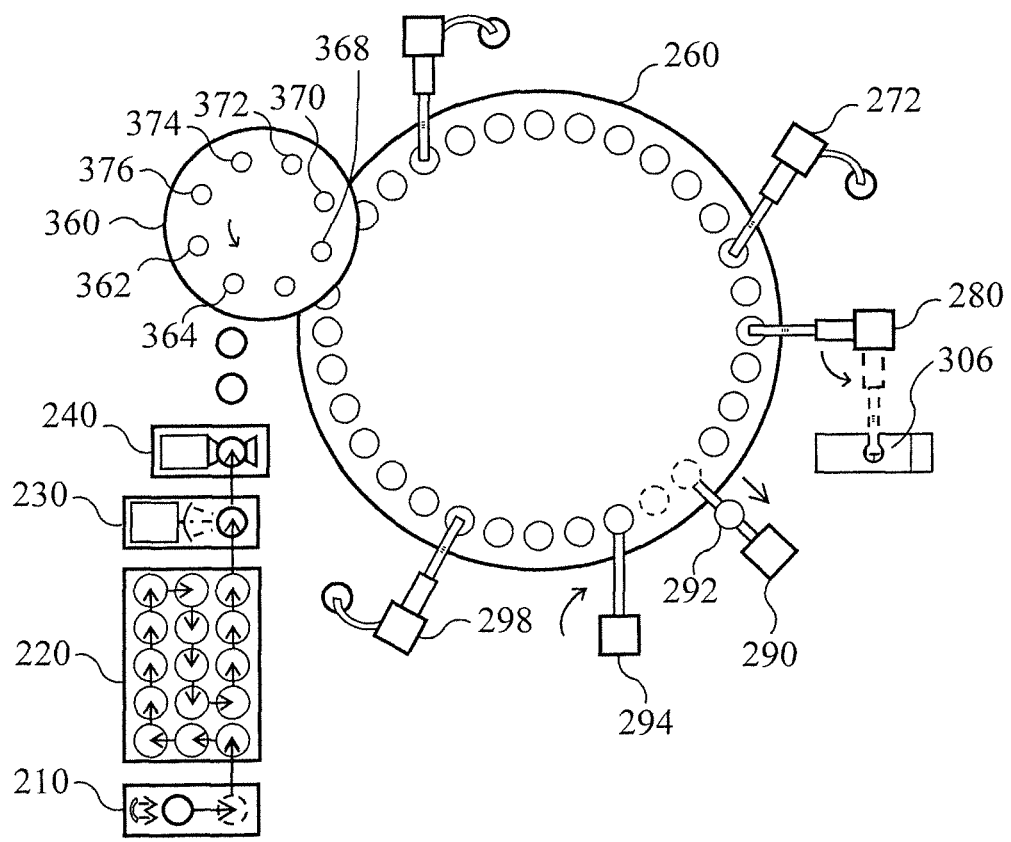
Figure 10A:
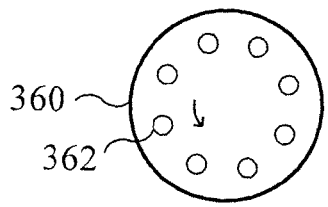
Figure 10B:
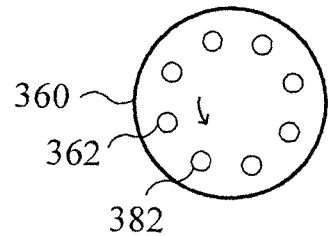
Figure 10C:
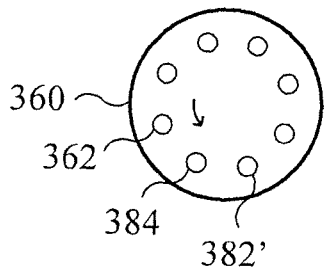
Figure 10D:
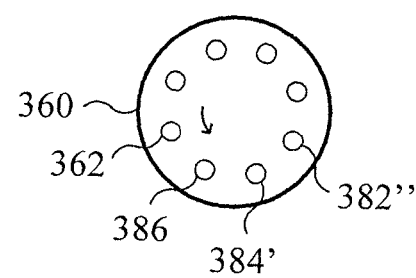
Figure 10E:
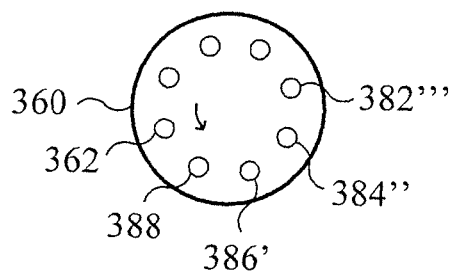
Figure 10F:
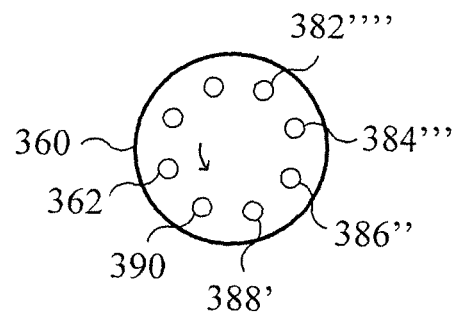
Figure 10G:
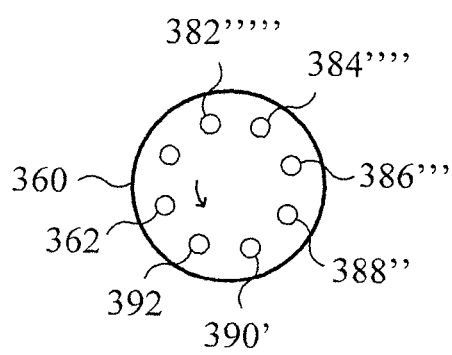
Figure 10H:
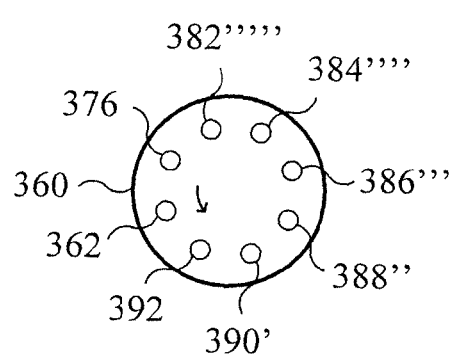
Figure 11:
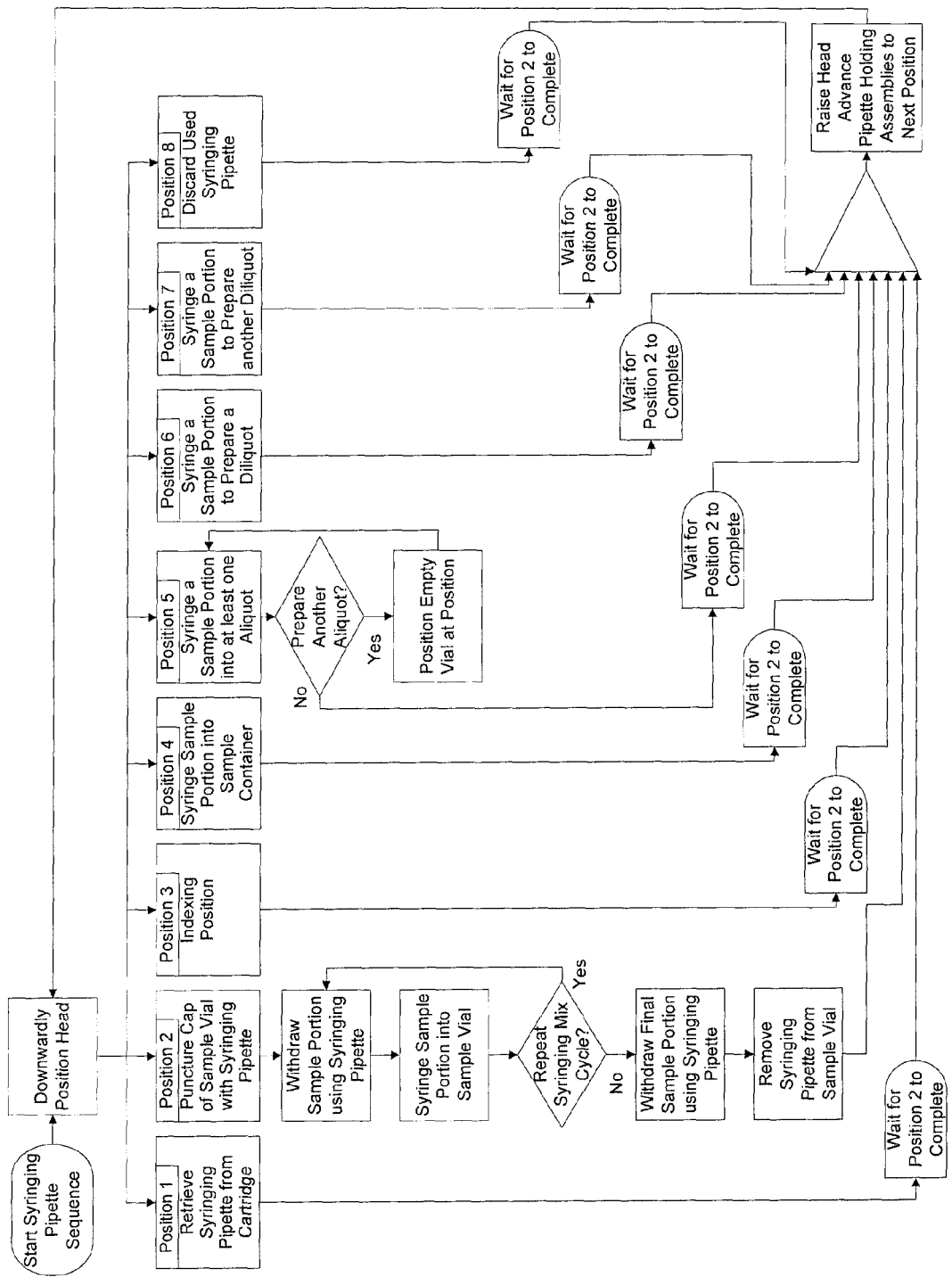
Figure 14:
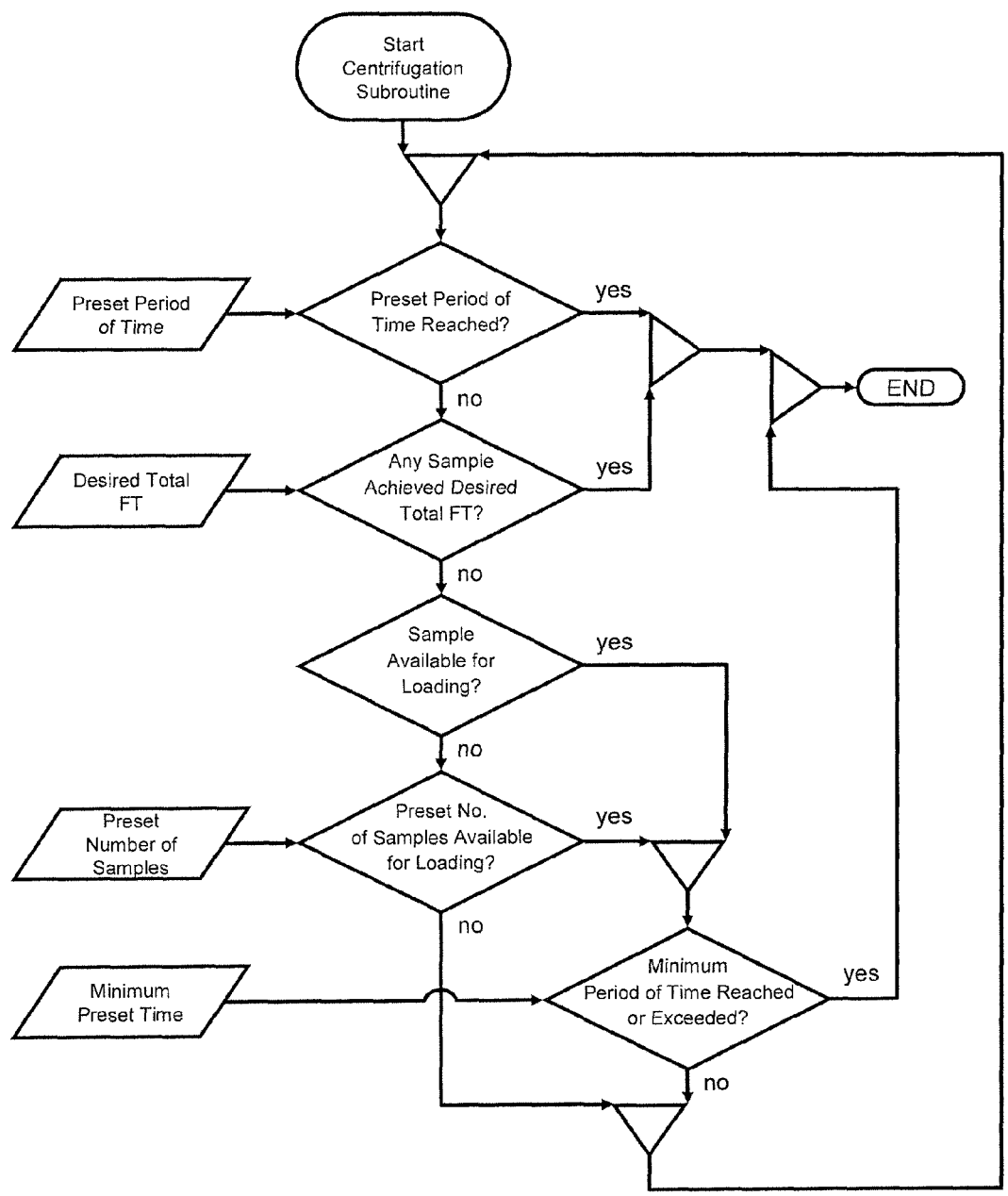
Figure 15:
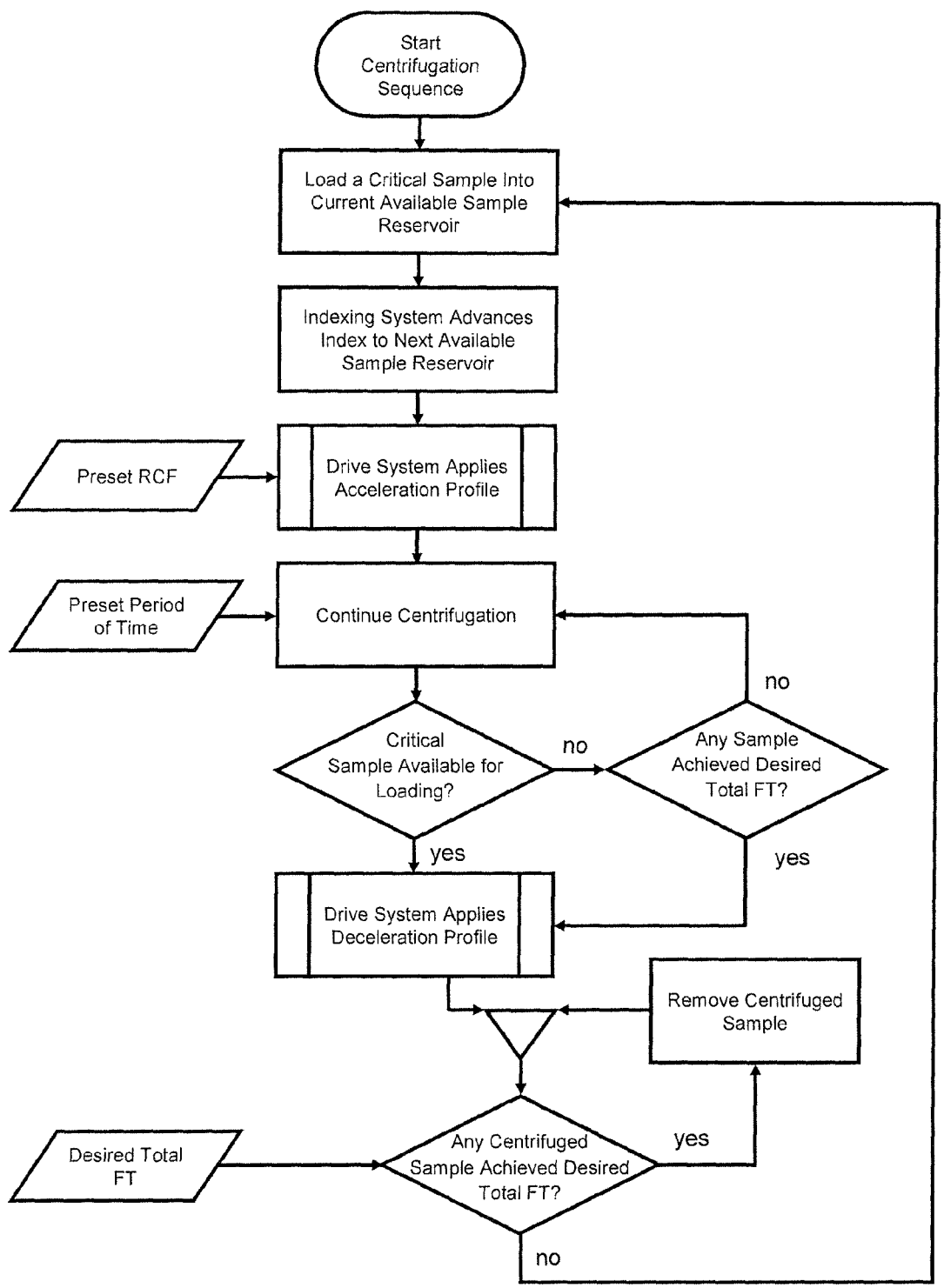
Figure 16A:
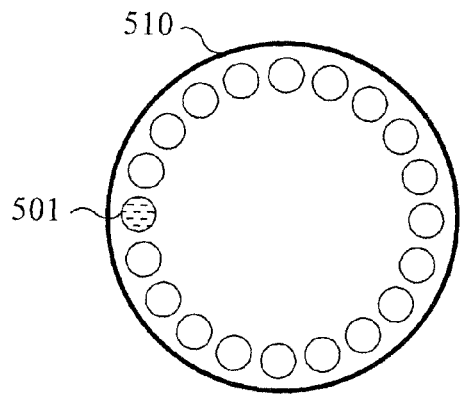
Figure 16B:
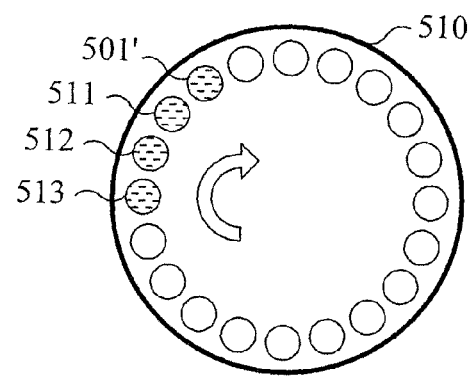
Figure 16C:
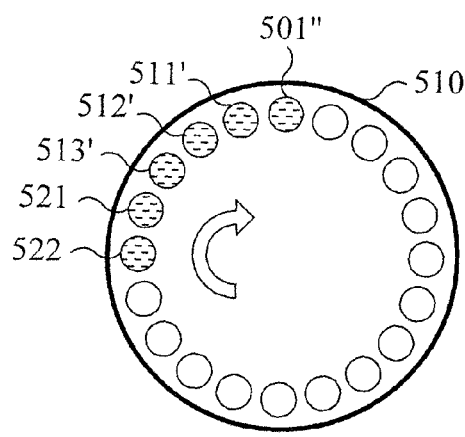
Figure 16D:
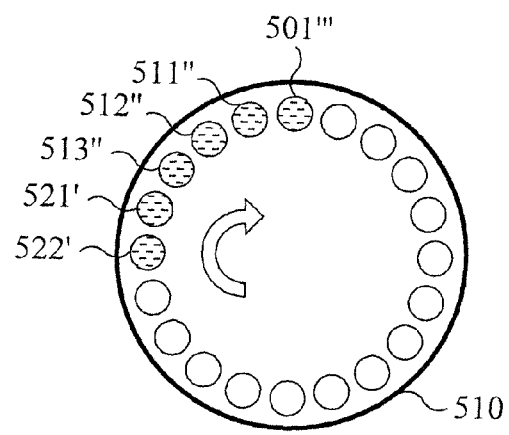
Figure 17A:
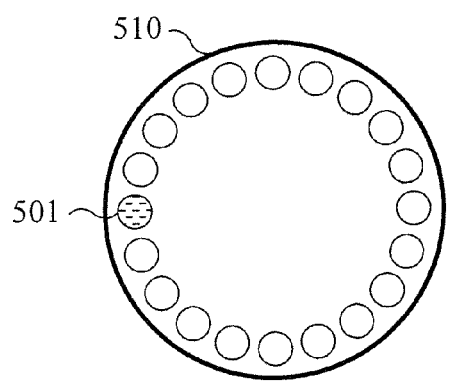
Figure 17B:
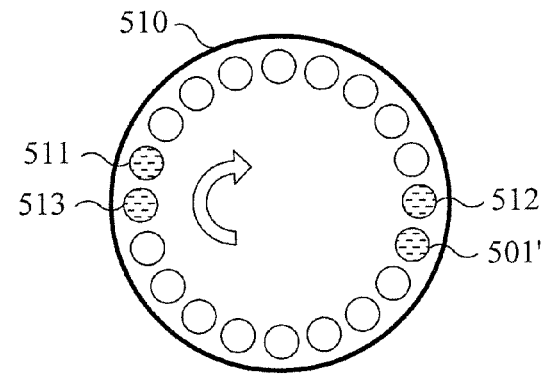
Figure 17C:
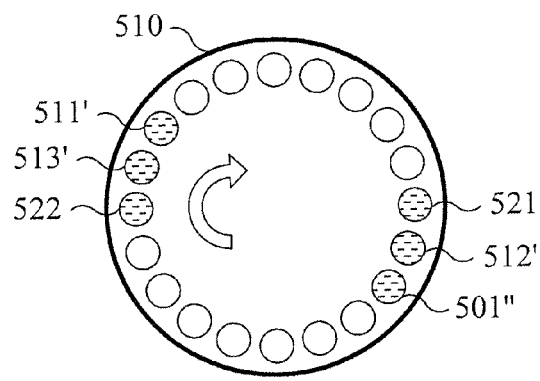
Figure 17D:
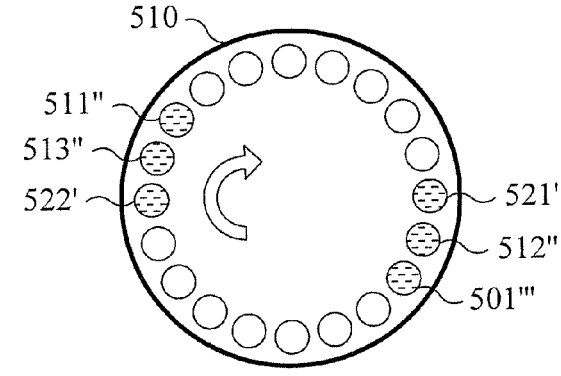
Figure 18:
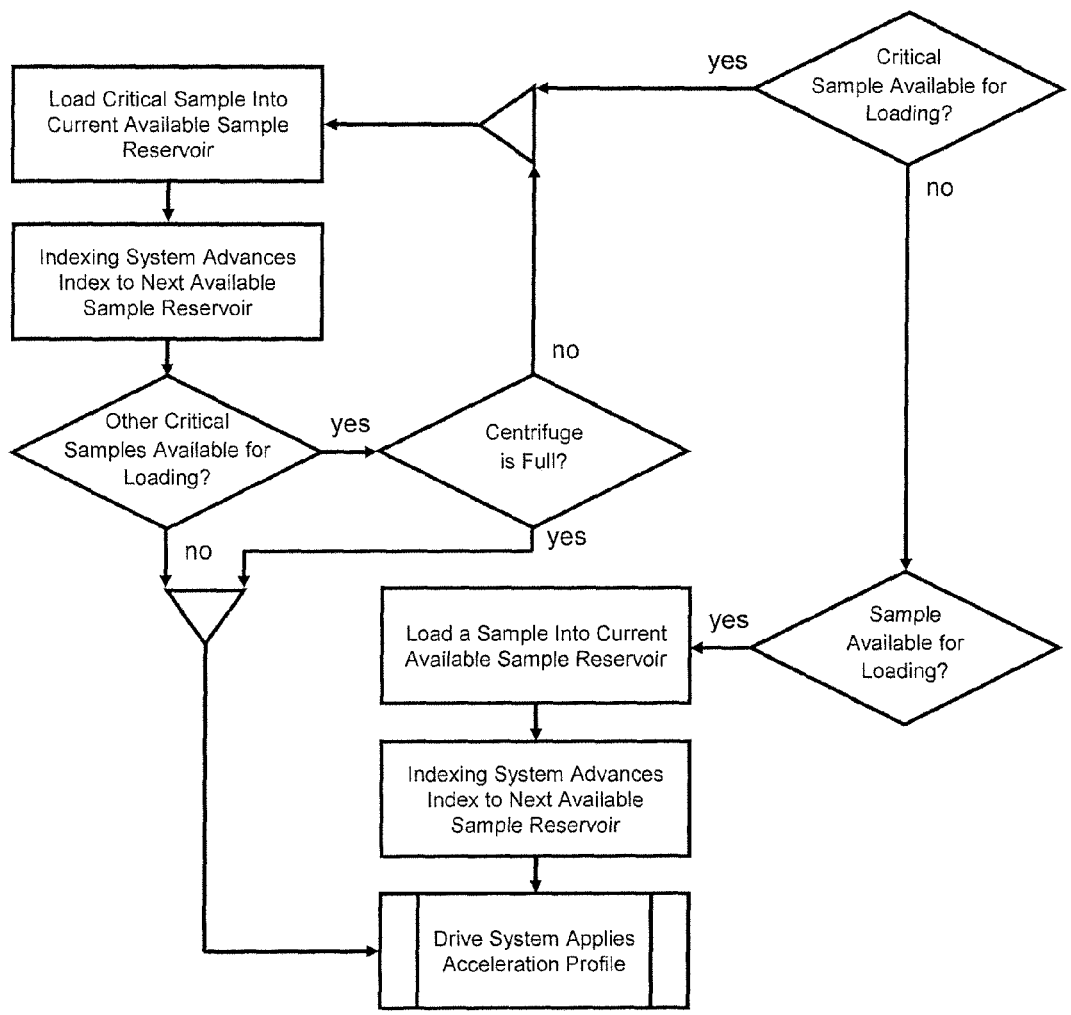
Figure 19:
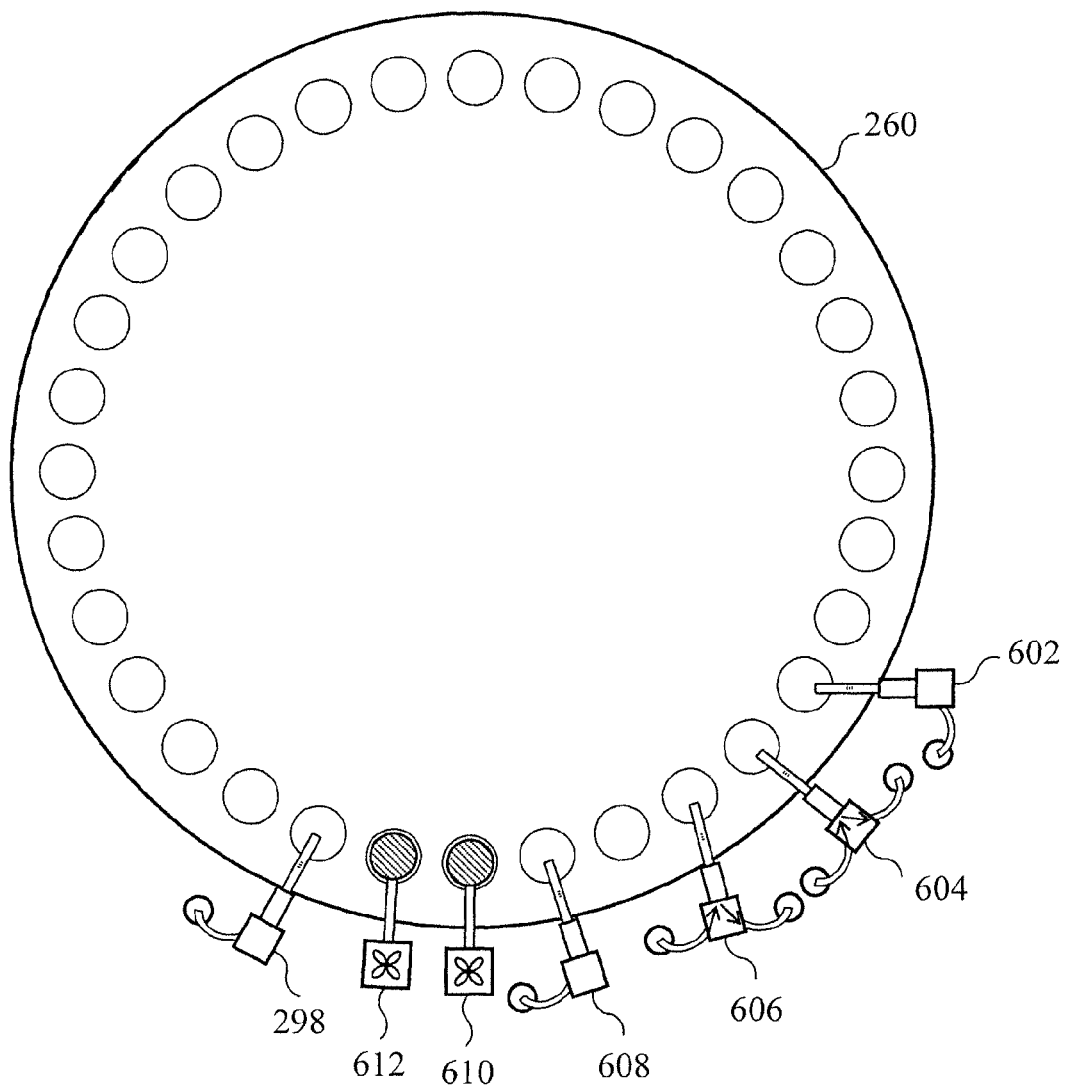
Figure 20:
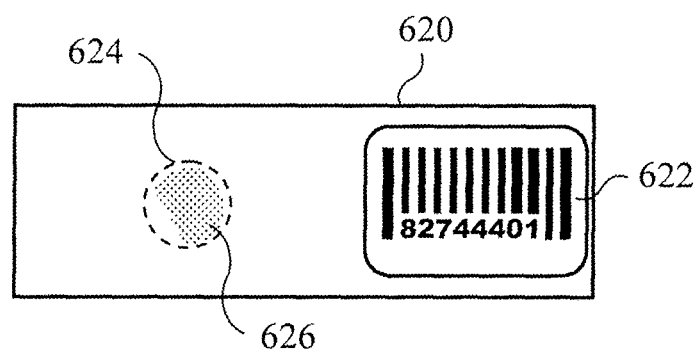

Having thus described the invention in general terms, reference will now be made to the accompanying drawings, which are not necessarily drawn to scale, and wherein:

FIG. 1 is a schematic plan view illustrating the general components of an integrated sequential sample preparation system having a sequential centrifuge;

FIG. 2 is a top plan view illustrating an embodiment of an integrated sequential sample preparation system having a sequential centrifuge;

FIG. 3 is a top view illustrating the sample infeed module of an embodiment of the integrated sequential sample preparation system;

FIG. 4 is a top view illustrating the sample infeed module of another embodiment of the integrated sequential sample preparation system useful for processing samples having various assigned priorities;

FIG. 5 is a top view illustrating the sample infeed module of another embodiment of the integrated sequential sample preparation system having a rotary holding device and a robotic arm;

FIG. 6 is a top view illustrating the syringing pipette module of an embodiment of an integrated sequential sample preparation system;

FIG. 7 is a section view taken along the VII-VII line of FIG. 6 showing a side view of the head of the syringing pipette module according to an embodiment of the invention;

FIG. 8 is a flowchart showing the steps of the syringing pipette module according to an embodiment of the invention;

FIG. 9 is a top view illustrating a sample transfer module for the inline preparation of aliquot and diliquot samples according to another embodiment of an integrated sequential sample preparation system;

FIGS. 10A, 10B, 10C, 10D, 10E, 10F, 10G, AND 10H are top plan views showing various positions of a sample transfer module according to another embodiment of the invention;

FIG. 11 is a flowchart showing the steps of the syringing pipette module according to another embodiment of the invention;

FIGS. 12A, 12B, 12C, and 12D are top plan views of a carousel used in certain embodiments of the invention showing four consecutive centrifugation sequences in an embodiment where a single sample is loaded in each centrifugation sequence in a position juxtaposed to a sample reservoir where a prior sample has been loaded;

FIGS. 13A, 13B, 13C, and 13D are top plan views of a carousel used in certain embodiments of the invention showing four consecutive centrifugation sequences in an embodiment where a single sample is loaded in each centrifugation sequence to maintain balance in the centrifuge;

FIG. 14 is a flowchart of an embodiment of the steps of a centrifugation cycle;

FIG. 15 is a flowchart of an embodiment of the steps of the centrifugation sequence for centrifuging a critical sample;

FIGS. 16A, 16B, and 16C are top plan views of a carousel used in certain embodiments of the invention showing three consecutive centrifugation sequences in an embodiment where one or more samples are loaded into the centrifuge during a centrifugation sequence in a position juxtaposed to a sample reservoir where a previous sample has been loaded;

FIG. 16D is a top plan view of a carousel used in certain embodiments of the invention showing an embodiment where there are no samples waiting to be loaded in a centrifugation sequence;

FIGS. 17A, 17B, and 17C are top plan views of a carousel used in certain embodiments of the inventive centrifuge showing three consecutive centrifugation sequences in an embodiment where one or more samples are loaded into the centrifuge in a centrifugation sequence to maintain balance in the centrifuge;

FIG. 17D is a top plan view of a carousel used in certain embodiments of the inventive centrifuge showing an embodiment where there are no samples waiting to be loaded in a centrifugation sequence;

FIG. 18 is a flowchart of an embodiment showing the steps for determining whether there is a critical sample that is to be loaded in the centrifuged;

FIG. 19 is a top plan view of a carousel used in certain embodiments of the invention showing an exemplary clean-in-place procedure for a centrifuge sample container; and FIG. 20 is a top view of a slide, according to an embodiment of the invention, with a sample dispensed thereon.

DETAILED DESCRIPTION OF THE INVENTION

The present invention now will be described more fully hereinafter with reference to the accompanying drawings, in which some, but not all embodiments of the inventions are shown. Preferred embodiments of the invention may be described, but this invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments of the invention are not to be interpreted in any way as limiting the invention.

Like numbers refer to like elements throughout. As further adopted herein, a number referencing a sample without a prime notation generally refers to the sample being subject to a single centrifugation sequence, a number referencing a sample with a single prime notation "'" generally refers to the sample being subject to a second centrifugation sequence, a number referencing a sample with a double prime notation "''" generally refers to the sample being subject to a third centrifugation sequence, and a number referencing a sample with a triple prime notation "'''" generally refers to the sample being subject to a fourth centrifugation sequence.

Many modifications and other embodiments of the invention set forth herein will come to mind to one skilled in the art to which this inventions pertain having the benefit of the teachings presented in the descriptions herein and the associated drawings. Therefore, it is to be understood that the inventions are not to be limited to the specific embodiments disclosed and that modifications and other embodiments are intended to be included within the scope of the appended claims.

As used in the specification and in the appended claims, the singular forms "a", "an", and "the" include plural referents unless the context clearly indicates otherwise. For example, reference to "a sample" includes a plurality of such samples.

It will be understood that relative terms, such as "radially" or "circumferentially" or "bottom" or "top" or the like, may be used herein to describe one element's relationship to another element as illustrated in the Figures. It will be understood that relative terms are intended to encompass different orientations of the articles in addition to the orientation as illustrated in the Figures. It will be understood that such terms can be used to describe the relative positions of the element or elements of the invention and are not intended, unless the context clearly indicates otherwise, to be limiting.

Embodiments of the present invention are described herein with reference to various perspectives, including cross-sectional and perspective views that are schematic representations of idealized embodiments of the present invention. As a person having ordinary skill in the art to which this invention belongs would appreciate, variations from or modifications to the shapes as illustrated in the Figures are to be expected in practicing the invention. Such variations and/or modifications can be the result of manufacturing techniques, design considerations, and the like, and such variations are intended to be included herein within the scope of the present invention and as further set forth in the claims that follow. The articles of the present invention and their respective components illustrated in the Figures are not intended to illustrate the precise shape of the component of an article and are not intended to limit the scope of the present invention.

Although specific terms are employed herein, they are used in a generic and descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

The invention described herein relates to an integrated sequential sample preparation system, specifically, an integrated sequential sample preparation system that is an integrated sequential centrifuge having a sequential centrifuge. The integrated sequential sample preparation system is generally comprised of an accessioning module, at least one sample identification module, a vortexing module, a sample transfer module, a sequential centrifuge, at least one extraction module, a centrifuged sample transfer module, a centrifuged container processing module, and an assay device processing module. In an embodiment of the invention, the assay device is a slide and the assay device module includes a slide transfer module; optionally, a slide preparation module; and a slide racking module. Optionally, an analyzer may be included as part of the integrated sequential sample preparation system or may be a separate device that analyzes the assay device prepared using the inventive integrated sequential sample preparation system. In other embodiments of the invention, the integrated sequential sample preparation system may include a sample queue for sorting and prioritizing samples. Without intending to be limiting, the inventive system can be particularly useful for preparing and/or processing a sample taken from a human or animal subject such as a cytological sample. Indeed, the inventive system may be used to prepare and/or process any discrete sample that needs to be separated into its component parts with at least one of the component parts undergoing subsequent analysis.

Without intending to be bound by theory, the invention provides improvements over conventional sample preparation systems known in the art by reducing dwell time through reducing the amount of time any sample must wait before being processed, increasing system throughput by reducing or eliminating the idle time within the various modules of the system, decreasing the area occupied by the system footprint by reducing the size requirements for the various modules and reducing the amount of space needed for sample preparation, and improving precision of the analytical process by more accurately processing a sample into a desired component required for analysis. In certain preferred embodiments, the invention provides improvements over conventional sample preparation systems known in the art by allowing critical and/or non-standard samples that need immediate and/or special processing to intervene in the normal processing of samples without a substantial loss in the efficiency of the operation. Other problems associated with conventional sample preparation systems known in the art that the inventive system resolves, in certain embodiments, includes reducing the considerable training requirements needed in order to use the system, reducing the number of disposables required per sample processed, providing chain of custody for a sample as it progresses through the process, providing the ability to easily interface to a laboratory information system, and reducing the amount of sample needed to produce the desired assay.

A schematic of a general embodiment of the integrated sequential sample preparation system in one aspect of the invention is shown in FIG. 1. In this illustrative embodiment of the invention, the integrated sequential sample preparation system 1 comprises an accessioning module 10. The term "accession," "accessioning," or any variation thereof used interchangeably herein means to assign a unique identification (hereinafter "ID") to the sample. Without intending to be limiting, the assigned ID will be useful for tracking the sample as it progresses through the various stages of processing up to and, in some embodiments, including the final analysis.

Preferably, the accessioning module will apply an indicia of reference or other means for identifying the sample to any of the sample containers holding the sample, as needed, and, in particular and preferentially, to the assay device where the prepared sample portion to be analyzed is disposed. Such indicia of reference or other means for particularly identifying the sample can be, for example, a visual means of inspection, a bar code, some symbolic means that can be visually and/or automatically detected such as with color schemes or some other structure identification, a magnetic electronic surveillance device such as a magnetic strip, a radio frequency tag, and other similar devices. Additionally, the inventive system has the capability to track and identify the sample as it progresses through the system anytime after the sample has been accessioned.

In an embodiment of the invention, the sample to be processed is removed from a collection device, such as a swab, broom-type sampling device, or brush, prior to accessioning. The means by which the sample is removed can be a manual procedure but, more preferably, an automated procedure in order to avoid sample contamination. In other embodiments of the invention, the sample to be accessioned is a fluid already contained in a sample vial. Preferably, the sample collection process is a direct-to-vial collection method to further minimize human contact with the sample and to prevent sample contamination.

The integrated sequential sample preparation system 1 further comprises a sample infeed module 20. The sample infeed module 20 is a handling module and, optionally, a holding area or a queuing area for samples that are to be prepared and processed by the integrated sequential sample preparation system 1. The sample infeed module 20 may be used, in certain embodiments of the invention, for other purposes. Such other purposes include providing the ability of the integrated sequential sample preparation system 1 to more easily handle critical or STAT samples that require priority preparation as well as other uses as further disclosed herein.

The integrated sequential sample preparation system 1 may further comprise a sample identification module 30. Alternatively, the integrated sequential sample preparation system 1, in certain embodiments of the invention, may comprise more than one sample identification module 30 positioned strategically throughout the integrated sequential sample preparation system 1. Without intending to be limiting, a plurality of sample identification modules 30 may be particularly useful for sample preparation systems that either periodically or routinely process critical samples that require a high degree of sample tracking and validation. A sample identification module 30, or plurality thereof, can also be useful for reporting the status of a sample to a central processing unit such as a laboratory information management system (hereinafter "LIMS"). The proper selection of the type of sample identification module used will be determined, of course, by the type of indicia of reference or other device for identifying the sample that is being used by the system.

The integrated sequential sample preparation system 1 can also comprise a vortexing module 40. The vortexing module 40 is primarily comprised of a vortex mixer. Vortex agitation ensures, among other things, that a sample is substantially mixed and any solids are substantially dispersed prior to dispensing at least a portion of the sample in a sample container that is to be sequentially centrifuged. Failing to vortex a sample or even improper vortexing of a sample can lead to erroneous results from the analysis of the sample. Proper vortexing also at least substantially disperses any particulate agglomerations, such as cell agglomerations in cytological samples, that may have formed since the sample was taken. The vortexing module 40 preferably includes a vortex mixer that will shake a vial holding the sample in a non-concentric circular motion to achieve the desired vortexing action.

Following vortexing, the sample is transferred to a sample container for processing in the sequential centrifuge 60 by a sample transfer module 50. Any system, device, procedure, or combination thereof, and as additionally disclosed herein, may be used to transfer either the entire sample or a portion thereof to a sample container to be centrifuged in the sequential centrifuge 60. The term "sequential centrifuge," as used herein, means a centrifuge that is capable of processing samples in a sequential manner. An exemplary sequential centrifuge is disclosed in U.S. Provisional Application 61/012,891 entitled "Sequential Centrifuge" to Fox et al., fully incorporated herein by reference. As further disclosed in the '891 provisional application and herein, a centrifuged sample or centrifuged sample portion is removed from the sequential centrifuge 60 by an extraction module 70. Additionally, in an embodiment of the invention, a centrifuged sample transfer module 80 is used to remove at least a portion, preferably at least a portion of a phase of, the centrifuged sample from the sample container in the centrifuge that is to undergo analysis and prepare an assay device using said centrifuged sample portion. Once the centrifuged sample portion is removed from the sample container in the centrifuge, the sample container is processed in the centrifuge container processing module 90. As disclosed herein, there are a number of centrifuge container processing modules that can be used to process the sample container. For example, in an embodiment of the invention, the centrifuge container processing module aspirates, cleans, rinses, dries, and any combination thereof the used sample container so that it can become available to centrifuge another sample. In another preferred embodiment of the invention, the centrifuge container processing module replaces the used sample container with a new sample container or a sample container that was cleaned and disinfected remotely wherein another sample that is to be centrifuged is loaded.

In the exemplary embodiment of the integrated sequential sample preparation system 1 illustrated in the schematic of FIG. 1, the assay device is a slide. In certain embodiments of the invention, when the assay device is a slide, the sequential sample preparation system 1 further comprises a slide transfer module 100. Optionally, the slide transfer module 100 can transfer the prepared slide to a slide preparation module 110. A slide racking module 120 may optionally be used to assemble the prepared slides. In other embodiments of the invention, the prepared slide is sent directly to an analyzer for analysis. In certain embodiments of the invention, the sequential sample preparation system 1 may also include the analyzer 130.

FIG. 2 illustrates an exemplary embodiment of an integrated sequential sample preparation system whose arrangement approximates, in certain relevant parts, the schema illustrated in FIG. 1. In this representative embodiment of the invention, the integrated sequential sample preparation system 201 includes an accessioning module 210. A sample is accessioned and, optionally, some indicia of reference or other device for identifying the sample is applied to the sample vial holding the sample at the accessioning module 210. Preferably, a similar indicia of reference or other device for identifying the sample is later applied to the assay device or slide that is to hold the final prepared sample portion that is to undergo analysis. From the accessioning module 210, the sample is placed into the sample infeed module 220 where the sample is queued for further processing.

A sample identification module 230 may be positioned to confirm the sample has been properly identified and, optionally, to ensure the sample portion is from the appropriate sample at the time an assay device is prepared with the extracted portion of the sample. In an embodiment of the invention, the sample identification module 230 visually scans the sample vial, container, other holding device, or assay device for the indicia of reference. In another embodiment of the invention, the sample identification module 230 employs an electronic means for reading the indicia of reference or other device for identifying the sample in order to identify the sample contained therein or disposed thereon. In other embodiments of the invention, the sample identification module 230 can employ more than one scanner, reader, or the like, and any combination thereof for identifying the sample. Without intending to be limiting in any way, such embodiments can be useful to provide redundancy in the sample identification module 230. In other embodiments of the invention, the integrated sequential sample preparation system 201 comprises other sample identification modules 230 to provide continuous sample tracking if such tracking is so desired. Obviously, in this embodiment of the invention, some indicia of reference or other device for identifying the sample must be provided for each vial, container, other holding device, or assay device that contains the sample that is to be identified by a sample identification module 230.

The sample is directed from the sample infeed module 220; optionally, through the sample identification module 230; and on to the vortexing module 240 where the sample is subjected to vortex agitation. Without intending to be bound by theory, vortexing ensures the sample is well-mixed and any solids are well-dispersed prior to dispensing at least a portion of the sample using a sample transfer module 50 into a sample container of the sequential centrifuge 260.

The sample transfer module 50 of the sequential sample preparation system 201 represented in FIG. 2 is a pipette syringing assembly 250. The pipette syringing assembly 250 includes a head 252 having a holding assembly for retrieving a syringing pipette from the syringing pipette cartridge 254, the syringing pipette cartridge 254 capable of holding a plurality of syringing pipettes. The syringing pipette rotates to a sample vial where the syringing pipette optionally can syringe the sample several times to ensure the sample is well-mixed before withdrawing and retaining at least a portion of the sample contained in the sample vial. The syringing pipette, with at least a portion of the sample contained therein, rotates to a position where its body is substantially aligned in parallel with a sample container in the sequential centrifuge 250. The tip of the syringing pipette is proximal to the opening of the sample container, and the syringing pipette syringes, preferably layers, the retained sample portion into the sample container. Finally the used syringing pipette rotates to a position where the pipette is discarded.

After the sample container with at least a portion of the sample contained therein undergoes at least one centrifugation sequence in the sequential centrifuge 260, a portion of the centrifuged sample may be removed by an extraction module 70 such as an aspirator 270. Optionally, after undergoing at least one other centrifugation sequence, a portion of the centrifuged sample may be removed by another extraction module 70 such as another aspirator 272. Optionally, other additional centrifugation sequences and aspiration sequences may be applied as needed (not shown).

In a preferred embodiment of the invention, the amount of time the sample is centrifuged is minimized in order to produce only the volume of a centrifuged sample portion needed for further analysis. Without intending to be bound by theory, minimizing the amount of time the sample is centrifuged can be particularly useful when high throughput sample processing is desired.

Once centrifugation is complete, a centrifuged sample transfer module 80 is used to transfer the centrifuged sample portion to an assay device. In one embodiment of the invention, the centrifuged sample portion is a supernatant. In another embodiment of the invention, the centrifuged sample portion is a sedimentary layer. Indeed, any layer or, less preferably, combinations thereof may be transferred to an assay device by the centrifuged sample transfer module 80. In the exemplary embodiment illustrated in FIG. 2, the centrifuged sample transfer module 280 retains at least a portion of a phase of the centrifuged sample and transfers and deposits said portion to an assay device. In this exemplary embodiment of the invention, the assay device is a slide.

The centrifuge container processing module 90 of the integrated sequential sample preparation system 201 illustrated in FIG. 2 includes a sample container removal assembly 290 for removing a used sample container 292 from the sequential centrifuge 260. A sample container transport mechanism 294 retrieves a sample container from a sample container cartridge 296, transfers the retrieved sample container to an empty sample reservoir in the sequential centrifuge 260, and places the retrieved sample container in the empty sample reservoir of the sequential centrifuge 260. Optionally, a density gradient medium may be added to a sample container by a density gradient transfer assembly 298. In another embodiment of the invention, the density gradient medium is predisposed in a sample container that is placed in the sequential centrifuge 260 by the sample container transport mechanism 294. In other embodiments of the invention, the sample container remains substantially free of a density gradient medium.

In another embodiment of the invention, the centrifuge container processing module 90 may include a series of aspirating, washing, rinsing, and drying steps (not shown) in any combination to allow the sample container to be reused without the need to replace the used sample container in the sequential centrifuge 260.

As disclosed herein, the assay device that is a slide may be specially prepared to promote adhesion of the deposited sample portion. In a preferred embodiment of the invention, an indicia of reference is applied to or some other device for identifying the sample is dispatched on the assay device as represented by the embodiment of the invention shown in FIG. 2. Such indicia of reference or other device for identifying the sample consigned to the slide 302 can be identified by a sample identification module 230 and associated with the ID assigned by the accessioning module 210.

The slide management system 300 of the integrated sequential sample preparation system 201 transfers a slide 306 from the slide cartridge 304 to the slide transfer module 308. The sample transfer module 280 deposits the desired portion of the centrifuged sample onto the slide 306. Optionally, the slide 306 includes a well for holding the centrifuged sample portion that has been transferred to the slide 306. Preferably, the slide 306 includes a material that allows the centrifuged sample portion to become adhered to the slide 306. Preferably, the slide transfer module 308 is sized such that it holds a sufficient number of samples for a given anticipated processing time for each of the samples such that the centrifuged sample portion deposited on the slide has a sufficient amount of time to become adhered to the slide 306 before any additional slide processing occurs. Optionally, the slide transfer module 308 may direct the slide 308 to a slide preparation module 110. Optionally, a cover may be placed over a portion of the surface of the slide 308. In an embodiment of the invention, a cover may be placed over a well that is present on the slide 306 to, among other things, confine the centrifuged sample portion to the slide 306. A slide racking module 320 may be use to rack the prepared slide 306. Optionally, the slide 306 may be transferred directly to an analyzer (not shown) for analysis.

The layout of the various modules as shown in the schematic of FIG. 1 and the illustration of FIG. 2 should not be considered as limiting. A person skilled in the art with the benefit of this disclosure would understand that any layout of the modules in the footprint of the inventive device is possible. Indeed, in certain embodiments of the invention, the modules may be placed in more than one footprint and still operate in an integrated sequential manner. All such configurations are intended to be part of this disclosure.

The accessioning module of the current invention assigns a unique ID to a sample and, optionally, applies an indicia of reference or other means for identifying the sample to the sample vial, container, other holding device, or assay device. Optionally, a similar indicia of reference or other means for identifying the sample may be applied to other sample vials, containers, holding devices, assay device, and any combinations thereof to provide automated tracking of the sample as it proceeds through the integrated sequential sample preparation system. A sample that has been accessioned provides the system a means by which to map the progress of the sample and provide chain-of-custody validation of sample results if needed. The ID assigned to the sample can merely be an ID assigned to the sample by the forwarding hospital, clinic, or other medical provider. In an embodiment of the invention, the ID is uniquely assigned by the accessioning module based upon an assignment procedure configured for the module that is characteristic of the laboratory that processes the sample. In another embodiment of the invention, the ID is an internal assignment that the laboratory where the sample is prepared uses merely for tracking the sample. Irrespective of the method for assigning the ID to the sample, the integrated sequential sample preparation system can provide the means by which the ID is be cross-matched to the sample that is prepared by the system.

The indicia of reference or other means for particularly identifying the sample can be, for example, a visual means of inspection, a bar code, some symbolic means that can be visually and/or automatically detected such as with color schemes or some other structure identification, a magnetic electronic surveillance device such as a magnetic strip, a radio frequency tag, and other similar devices. Some non-limiting examples of the types of indicia of reference or other means for identifying the sample can be found in U.S. Pat. No. 5,592,948 entitled "Self Contained Vial for Drawing, Storing, Sealing and Identifying a Fluid Sample" to Gatten (bar code), U.S. Pat. No. 7,091,864 entitled "Sample Container with Radiofrequency Identifier Tag" to Veitch et al. (RFID), U.S. Pat. No. 7,258,840 entitled "Sample Vial with Transponder" to Maas et al. (transponder device).

The ID assigned to the sample by the accessioning module becomes associated with the sample and may be used to gain access to other information concerning the sample. Non-limiting examples of other information include type of sample; origin of the sample; identification number assigned by the originator of the sample; instructions for handling the sample; billing information; date the sample was taken; date when results are desired; information relating to the human or animal from which the sample was taken; other samples associated with the sample, if any; criticality of the sample; type of results desired for and/or analyses to be performed on the sample; and any combination thereof.

After the sample has been accessioned, it is directed to the sample infeed module. A non-limiting use of the sample infeed module is to provide a queue where samples waiting for further preparation in the sequential sample preparation system are held. Any number of configurations of the sample infeed module are possible depending on the objectives that are desired to be achieved. For example, one purpose of the sample infeed module is merely to act as a short-term holding area for samples that are awaiting further processing. In an embodiment of the invention, the sample infeed module is designed to hold the number of samples expected to accumulate, especially during peak sample processing intervals. However, an advantage of the integrated sequential sample preparation system is its ability to avoid the accumulation of a large number of samples waiting in the sample queue that is otherwise experienced in systems having modules that process in batch mode. Therefore, without intending to be limiting, the size needed for any sample holding area can be expected to be smaller than that required for conventional preparation systems. FIG. 3 is a schematic of a sample infeed module according to an embodiment of the invention. The sample enters the sample infeed module 220 at the entry point 222 and sequentially progresses internally through the module at a plurality of sample positions 224. The sample leaves the sample infeed module at exit point 226 and progresses to the next module.

A sample may progress through the sample infeed module 220 using any means capable of conveying the sample. The sample may be conveyed in the sample infeed module 220 by, for example, manual procedures, methods, and systems; automated procedures, methods, and systems; and any combination thereof. In an embodiment of the invention, a person advances the samples through each of the sample positions of the sample infeed module 220. In another embodiment of the invention, a robot arm advances the samples through each of the sample positions of the sample infeed module 220. In another embodiment of the invention, the samples are conveyed through the sample infeed module 220. In yet another embodiment of the invention, the sample infeed module 220 has partitioned pathways and the samples progress through each of the sample positions by a combination of gravity and a series of movements undertaken by the sample infeed module 220.

In another embodiment of the invention, the sample infeed module partitions samples among other samples having similar characteristics. The sample infeed module can make such determinations using the information provided by the accessioning module as disclosed herein. FIG. 4 illustrates an embodiment of a sample infeed module that partitions a sample among other samples having, for example, the same priority for processing in the integrated sequential sample preparation system. A sample enters the sample infeed module 330 at the entry point 332. Samples having the highest priority for processing are diverted from the normal sequential path of conveyance at the first sample position 334 and sequentially are progressively conveyed to the last critical sample position 340. Samples having an intermediate priority for processing are diverted from the normal sequential path of conveyance at the second sample position 336 and sequentially are progressively conveyed to the last intermediate sample position 342. Other samples having routine priority or any priority less than samples having an intermediate priority are conveyed along the normal sequential path of conveyance starting at third sample position 338 towards the last sample position in the normal path of conveyance 344. Once a sample has reached this position, it may exit the sample infeed module 330 at the exit point 346 progressing directly through the last intermediate sample position 342 and the last critical sample position 340. However, if any sample is waiting to be processed in the intermediate priority queue represented by any sample position between the second sample position 336 and progressing directly therefrom to the last intermediate sample position 342, inclusive, then this sample will leave the sample infeed module 330 at exit point 346 progressing directly through the last critical sample position 340 as long as there are no critical samples waiting to be processed. If any sample is waiting to be processed in the critical priority queue represented by any sample position between the first sample position 334 and progressing directly therefrom to the last critical sample position 340, inclusive, then this sample will leave the sample infeed module 330 at exit point 346 ahead of any lower priority samples waiting to be processed.

A sample infeed module may include any number of special handling queues based on any number of requisite priority assignments. Optionally, other categories of sample groupings can be partitioned in a similar manner. Samples may be partitioned by, for example, analysis type, customer number, total amount of time a sample is to be centrifuged, and any combination thereof.

Other configurations of sample infeed modules are possible. In another embodiment of the invention, a sample infeed module comprises a rotary holding device, a robot arm, and a controller for positioning the rotary holding device and robot arm over a sample holding position. Once in position, the controller instructs the robot arm to retrieve the sample in that position and transport that sample to the next module in the integrated sequential sample preparation system. In another embodiment of the invention, the robot arm is itself movable on a cam. Depending on its position on the cam, the robot arm may be provided with axial movement capability, radial movement capability, and any combination thereof. Preferably, the robot arm is capable of moving in the vertical direction in order to enable the arm to move in a downward direction to retrieve a sample and then in an upward direction to move the retrieved sample to another position in the rotary holding device or on to the next preparation module. In other embodiments of the invention, the rotary holding device is capable of moving in a vertical direction allowing the rotary holding device to move upward in the axial direction to allow the robot arm to retrieve the sample and in a downward direction to return to its normal resting position once the sample has been retrieved.

FIG. 5 shows an embodiment of the invention where the sample infeed module includes a rotary holding device 350, a plurality of sample positions 352 where samples are conveyed by movement of the rotary holding device 350 and a robot arm 354, the robot arm 354 movably affixed to a cam assembly 356 equipped with a stepper motor and is further rotatably affixed to the cam assembly 356 for moving samples into and away from the rotary holding device 350. The operation of the rotatable and, if so equipped, the axial movement of the rotary holding device 350 and rotatable and horizontal movement of the robot arm 354 is preferably controlled by a controller 358. Optionally, each of the sample positions may be provided with a slot for exposing an indicia of reference or other device for identifying the sample. A sample identification module may be used to provide feedback to the controller 358 regarding the positions of the samples. Exemplary devices having a rotating wheel for holding samples with such samples identified by a barcode scanner can be found in U.S. Patent Publication Nos. 2004/0258565 and 2006/0210435.

In other embodiments of the invention, the controller 358 has an indexing system for tracking the position of each sample. In another embodiment of the invention, each of the samples introduced to the sample infeed module can be identified to the controller 358 as having a certain priority. The controller 358 will cause the higher priority samples to be removed from the rotary holding device 350 before any lower priority samples are removed from the rotary holding device 350. In yet another embodiment of the invention, the controller 358 partitions the samples by some other category allowing the samples to be removed according to the categorical grouping.

"Sample" as used in the context of the discussion for sample movement can mean an individual sample itself that is moved from position to position by a transfer assembly. A non-limiting example of a transfer assembly includes the combination of an aspiration device for removing the sample from one sample container and a dispensing device for injecting the sample in another sample container. More preferably, "sample," as used in the context of the discussion for sample movement is a sample that itself is in a sample vial, container, or any other holder, with the sample vial, container, or any other holder being moved from position-to-position as disclosed herein.

Indeed any apparatus, method, system, process, procedure, and the like known or to be developed in the art may be used as a sample infeed module. For example, U.S. Pat. No. 6,902,703 entitled "Integrated Sample Processing Module" to Marquiss et al. discloses a transport module having a mechanism for shuttling a sample holder between various operational sites; U.S. Pat. No. 6,499,366 entitled "Sample Feeder" to Meadows et al. discloses a device for automatically feeding sample containers between various stations of an analyzer; and U.S. Pat. No. 4,647,432 entitled "Automatic Analysis Apparatus" to Wakatake discloses an exchange mechanism for reaction tubes at designated positions between a pair of turret tables.

In another embodiment of the invention, the inventive system comprises more than one sequential centrifuge and a sample infeed module directs a sample to one of the sequential centrifuges based upon at least one of number of samples waiting to be prepared, priority of the sample, type of centrifugation sequence the sample requires, type of analysis to be performed on the sample, balance in at least one of the sequential centrifuges, and availability of other modules downstream of the sample infeed module.

In another embodiment of the invention, the inventive system comprises more than one sample infeed module. Preferably, at least one of the sample infeed modules will act as a primary sample infeed module that directs samples to at least one other sample infeed module, e.g., a secondary sample infeed module. Inventive systems having a plurality of sample infeed modules may be useful in certain embodiments of the invention for, among other things, improving the management of samples in the inventive system, particularly in periods of peak processing demand; managing the preparation of samples when more than one sequential centrifuge or even when more than one preparation line is in use; segregating samples based upon priority or some other category; and any combination thereof.

Certain embodiments of the invention provide a sample identification module. Preferably, the sample identification module will be selected based upon the indicia of reference or other device for identifying the sample that is consigned by the system. For example, if the indicia of reference is a barcode, the sample identification module is a barcode scanner. Barcode scanners that can be used in the inventive device include, but are not limited to, the BD IMAG™ barcode scanner or the BD BACTEC™ barcode scanner manufactured by BD (Becton, Dickinson, and Company) (Franklin Lakes, N.J. USA), the BIOMEK™ automated tube barcode reader manufactured by Beckman Coulter (Fullerton, Calif. USA), and the SCANARRAY™ $G_x$ Plus microanay scanner manufactured by Perkin Elmer Life and Analytical Sciences (Shelton, Conn. USA).

In certain embodiments of the invention, the sample vials are maintained in a position such that the barcode is always visible when substantially in view of the barcode scanner. In other embodiments of the invention, the sample vial is rotated so that the barcode scanner may read the barcode. In yet other embodiments of the invention, the barcode scanner itself rotatably moves about the sample vial, container, or holder so that the scanner can read the barcode. In yet other embodiments of the invention, the sample identification module includes more than one scanner positioned about the sample vial, container, or holding device allowing the applied barcode to be read by any one of the scanners. In a preferred embodiment of the invention, the barcode scanner is a multidirectional scanner allowing for the widest possible viewing area in scanning for a barcode. For example a multidirectional scanner can be a laser scanner such as that disclosed in U.S. Pat. No. 6,634,557 entitled "Multidirectional Barcode Reader" to Kocznar et al. or the dual laser scanner disclosed in U.S. Pat. No. 6,721,625 entitled "Barcode Dual Laser Scanner Targeting" to Mehlberg et al. Another example of a multidirectional scanner is the barcode reader disclosed in U.S. Pat. No. 6,547,140 entitled "Microwave Barcode Reader Using Dipolar Antenna" to Marchand.

The sample identification module of another embodiment of the invention can use other types of scanning systems including, but not limited to, an electronic magnetic scanner, a RF antenna transceiver, or a microprocessor based tracking system. Of course the indicia of reference or other device for identifying the sample that is consigned by the system must be commensurate with the type of scanner being employed. In certain embodiments of the invention, use of such scanning systems may be preferred. For example a scanning device that is a RF antenna transceiver for reading a RFID tag can eliminate the line-of-sight complications that can arise in certain embodiments of the invention that use a barcode scanner or magnetic reader. In a preferred embodiment of the invention, the vial holding the sample comprises a RFID tag, the accessioning module writes the necessary sample information to the RFID tag, and the sample identification module includes a RF antenna transceiver for reading the RFID tag to identify the sample. In an embodiment of the invention, the assay device will also comprise a RFID tag whereby the necessary sample identification information is also written. RFID tags have been used in other art segments for tracking samples. Non-limiting examples of such uses include RFID tags for chain of custody information to track gas samples disclosed in U.S. Pat. No. 6,769,316 entitled "Gas Cartridge for Gas Sampling Apparatus" to Rogers et al., RFID tags for sample identification disclosed in U.S. Pat. No. 7,275,682 entitled "Sample Identification Using RFID Tags" to Excoffier et al., and biological kits that utilize RFID technology disclosed in U.S. Patent Publication No. 2006/0199916 entitled "Compositions and Methods for Using Radio Frequency Identifiers in Biological Sciences" to O'Banion et al.

In other embodiments of the invention, the sample identification module includes at least two scanners. Such embodiments can be useful when redundancy is important in the sample identification process. In certain embodiments of the invention, the at least two scanners can be the same type of scanner. In yet other embodiments of the invention, the sample identification module includes at least two different types of scanners such as, for example, a barcode scanner and a RF tag reader. In this embodiment, of course, the system must consign at least two types of indicia of reference or other device for identifying the sample with the selection of such apposite to the choice of the types of scanners used in the module.

In tandem with the accessioning module and at least one sample identification module, the inventive system may also comprise a tracking system for providing chain of custody information for the processed samples.

Vortex mixing ensures, among other things, the sample is homogenously well-mixed, solid particulates are well-dispersed, and any particulate agglomerations that may have formed since the time the sample was taken become separated. Preferably, such mixing should be non-concentric and asymmetric in nature to prevent sedimentation of any suspended solids. Even more preferably, vortex agitation should be gentle enough to prevent damage to any diagnostically important material that is present in the sample.

In an embodiment of the invention, the vortexing module includes a motor, preferably a servomotor having a controller. The motor attaches to the distal end of a cylindrical-shaped motor shaft. In a preferred embodiment of the invention, the motor is a stepping motor. A transfer gear attaches at the diametrically opposite distal end of the motor shaft. The motor drives the motor shaft causing the transfer gear to rotatably turn. As the transfer gear turns, it drives a belt that in turn causes a drive gear to turn. The drive gear is attached to a distal end of a lower shaft that is attached to an upper shaft. A portion of the lower shaft and the upper shaft are enclosed in a shaft enclosure. In an embodiment of the invention, the upper shaft is rigidly affixed to the lower shaft such that when the lower shaft turns the upper shaft turns at the same angular velocity. In another embodiment of the invention, the upper shaft is affixed to the lower shaft with a transfer coupling such that when the lower shaft turns, the upper shaft can turn at an angular velocity that is different from the angular velocity of the lower shaft.

The distal end of an engagement shaft is affixed to a top surface of the upper shaft. Preferably, the engagement shaft is affixed at a position on the top surface of the upper shaft so that the engagement shaft is radially off-set from a centerline defined by an axial line that passes through the radial center of the upper shaft.

The vortexing module can further comprise a base plate and a support arm extending perpendicular to the base plate. A guide plate and support plate are attached to and extend perpendicular from the support arm. The guide plate defines a cavity through which the engagement shaft extends. In a preferred embodiment of the invention, a portion of the outer surface of the engagement shaft remains substantially in contact with the outer walls defining the cavity. In an embodiment of the invention, the cavity is substantially circular in cross section. In another embodiment of the invention, the cavity is substantially spherical in cross section and, as the lower shaft turns, a transfer coupling allows the angular velocity of the upper shaft to change to allow the engagement shaft to substantially maintain contact with the outer walls defining the cavity.

A holding device is attached to another distal end of the engagement shaft preferably by an attachment assembly that allows the holding device to become movably attached to the engagement shaft. In an embodiment of the invention, the attachment assembly for movably attaching the holding device to the engagement shaft is a ball and socket joint.

The engagement shaft extends through the cavity, preferably in a position offset relative the center line defined by the line passing through the center of the cavity. Some portion of the outer surface of the engagement shaft maintains contact with the surface defining the cavity as the engagement shaft is turned by the angular movement of the lower shaft. The holding device is movably attached to the distal end of the engagement shaft.

The holding device is designed to support a bottom portion of a sample vial. The sample vial is inserted through a passage in the support plate with the bottom of the sample vial being supported by the holding device. Preferably, the opening of the passage is defined by a recess so that as the engagement shaft causes the holding device to move in response to changes in position of the engagement shaft, the lower part of the sample tube also changes position but the upper portion remains in substantially the same position. Without intending to be bound by theory, the lower portion of the sample tube will move further away from the center line, defined by the line passing through the center of the passage, than will the upper portion of the sample tube relative to the same center line. Preferably, the opening of the passage is defined by a recess that allows the upper portion of the sample vial to remain substantially in the same axial position relative to the center line defined by the line extending through the center of the passage but without causing damage to the sample vial even as the lower portion of the sample vial moves in response to changes in the position of the holding device. Further, it is preferred that the surface defining the passage and recess is such that the frictional forces between said surface and the sample vial are minimized allowing for a change in angular position of the sample vial but without causing damage to the sample vial.

Optionally, the sample vial may include an annular ring positioned either at or substantially near the opening of the sample vial. The purpose of the annular ring, in some embodiments of the invention, is to further secure the sample vial in the passage.

In a preferred embodiment of the invention, a transfer coupling allows the angular velocity of the upper shaft to change to allow the engagement shaft to remain in contact with the outer walls defining the cavity and the cross section of the cavity is such that the motion imparted to the sample vial at the lower portion of the sample vial is moved by the holding device in a non-concentric circular motion. Without intending to be bound by theory, a non-concentric circular motion allows for a vortex to form in the sample contained in the sample vial.

It should be recognized by a person skilled in the art that this description of a vortex module is merely illustrative of an embodiment of vortex mixing. Other modules for vortex mixing either known or to be later disclosed may be used in the inventive integrated sequential sample preparation system and are intended to be part of this disclosure. For example, such other processes can be found in the disclosures in U.S. Pat. No. 3,944,188 entitled "Concentrating Vortex Shaker" to Parker et al. and U.S. Pat. No. 7,008,788 entitled "Containers for Supports Comprising Biopolymers" to Schremp et al. Other non-limiting examples of vortex mixers commercially available include the VWR™ Vortex Mixer and VWR Signature™ vortex mixers manufactured by VWR International (West Chester, Pa. USA); the fixed speed, analog, digital, and pulsing vortex mixers manufactured by Fisher Scientific (Pittsburgh, Pa. USA); and the VORTEX GENIE 2™ manufactured by Bender & Hobein (Zurich, Schwitzerland).

The invention further comprises a sample transfer module for loading a sample into a sample reservoir of the sequential centrifuge. There are a variety of means to accomplish loading a sample into the sequential centrifuge. A non-limiting example of sample loading can include a sample transfer system that removes a sample from a vial, container, or other holder and dispenses the sample into a sample container in the centrifuge. Such a sample transfer system can be accomplished by a variety of systems known in the art. An example of a sample transfer system includes, but is not limited to, an aspiration system and an injection system. Sample loading can include placing a sample container comprising the sample into the sequential centrifuge. The sample may be placed by a manual system and/or procedure, an automated system and/or procedure, and any combination thereof.

In an embodiment of the invention, the sample transfer module may use a pipette to transfer at least a portion of a sample contained, for example, in a sample vial into a sample container. In certain embodiments of the invention, the sample transfer module uses a pipette and involves at least one manual step. Non-limiting examples of manual pipettes are further discussed in U.S. Pat. No. 4,117,728 entitled "Pipette" to Johnson; U.S. Pat. No. 4,369,655 entitled "Manually Holdable Automatic Pipette" to Citrin; and U.S. Pat. No. 5,620,660 entitled "Pipette System" to Belgardt et al. Indeed any manual pipette now known or later invented could be suitable for use in certain embodiments of the invention disclosed herein.

In preferred embodiments of the invention, the sample transfer module is automated and uses a pipette to transfer at least a portion of a sample to a sample container. In certain preferred embodiments of the invention, the sample transfer module is automated and, in addition to sample transfer, also automates sample mixing and layering of the sample in a sample container. More preferably, the sample transfer module automatically mixes, transfers, and layers a desired amount if sample into a sample container. An example of an automated syringing pipette assembly that can be used in certain preferred embodiments of the invention include the PREPMATE manufactured by BD (Becton, Dickinson, and Company) (Franklin Lakes, N.J. USA). The PREPMATE system automatically mixes and removes the specimen from sample vials, preferably a SUREPATH™ preservative vial, also available from BD, and layers the specimen onto a density gradient medium. In a preferred embodiment of the invention, the density gradient medium is PREPSTAIN™ density reagent, also available from BD, disposed in a sample container. The PREPMATE system also allows for caps to remain on the sample vials during the operation, which is preferred because it reduces the possibility of sample contamination and prevents lab personnel from becoming exposed to the sample.

Preferably, any pipette used in a sample transfer module, whether the module is fully manual, in part manual, or automated, is disposable in order to eliminate the possibility of sample contamination.

In a preferred embodiment of the invention, the sample transfer module is a syringing pipette assembly that has a head assembly. The head assembly is extensible downward and returnable upward in a vertical plane. Further, the head assembly is rotatable in a horizontal plane. The head assembly moves downward in the vertical plane to at least one of retrieve a new syringing pipette and puncture a sample vial closure, and the head assembly moves rotatably in the horizontal plane between at least one of a syringing pipette retrieval station, a sample vial holding assembly, the current available sample reservoir, and a syringing pipette discard station.

FIG. 6 is top plan view illustrating an exemplary syringing pipette assembly useful in certain embodiments of the integrated sequential sample preparation system. The sample pipette syringing assembly 250 includes a head 252. The head 252 further includes a first position 256 where a syringing pipette is retrieved from a syringing pipette cartridge 254; a second position 257 where at least a portion of the sample is withdrawn from a sample vial; a third position 258 where the at least part of the portion of the sample withdrawn from the sample vial is syringed into a sample container; and a fourth position 259 where the used syringing pipette is discarded. The first position 256 is hereinafter described as the syringing pipette retrieval station, the second position 257 is hereinafter described as the sample extraction station, the third position 258 is hereinafter described as the sample syringing station, and the fourth position 259 is hereinafter described as the syringing pipette discard station.

A syringing pipette is retrieved from the syringing pipette cartridge 254 when in the syringing pipette retrieval station 256. In the sample extraction station 257, the syringing pipette retrieved in the syringing pipette retrieval station 256 is positioned such that the tip of the syringing pipette is substantially aligned with a cap of a sample vial, punctures the cap of the sample vial, and withdraws at least a portion of the sample contained therein. In a preferred embodiment of the invention, the syringing pipette withdraws a portion of the sample and syringes the withdrawn portion of the sample back into the sample vial to further mix the sample before finally withdrawing some of the sample contained therein. Even more preferably, the syringing pipette continues to withdraw a portion of the sample and syringe the withdrawn portion of the sample back into the sample vial at least one more time to further mix the sample before finally withdrawing at least a portion of the sample contained therein.

In the sample syringing station 258, the syringing pipette is positioned such that the tip of the syringing pipette is aligned with the opening of a sample container where the portion of the sample withdrawn at the sample extraction station 257 is syringed therein. Preferably, the sample portion is layered into the sample container that has included therein a density gradient medium. Finally, the used syringing pipette is discarded at the sample pipette discard station 259. These series of operations are more fully disclosed herein.

In a preferred embodiment of the invention, each of the stations of the syringing pipette assembly will function substantially simultaneously. For example, while a new sample pipette is retrieved in the syringing pipette retrieval station 256, a sample portion is extracted in the sample extraction station 257, another sample portion is syringed in the sample syringing station 258, and a used syringing pipette is discarded in the sample pipette discard station 259.

An automated syringing pipette system typically requires a syringing pipette that has been designed to specifically work with the system. Syringing pipettes that have been designed to specifically work with an automated system can be found in, for example, U.S. Pat. No. 4,830,832 entitled "Pipette and Pipetting Apparatus" to Arpagaus et al. The syringing pipette of an automated syringing pipette system generally comprises a piston assembly that includes a piston, piston channel, an annular seal, and a piston housing that interactively operate to draw liquid through the tip opening of a tip into a cylinder channel. The cylinder channel is defined by a cylinder wall of a cylinder. Without intending to be bound by theory, the upper portion of the piston is preferably tapered enabling the piston, hence the syringing pipette, to be more easily directed into and received by a syringing pipette holding assembly.

The piston channel is defined by the piston housing. The outer portion of the annular seal will have the proper dimensions and be constructed of a material that will allow it to be movable but remain in substantial contact with the inside wall of the piston housing. Without intending to be bound by theory, as the piston is drawn in an upward direction, the annular seal is drawn upward into the piston channel allowing a vacuum to form within the cylinder channel when the tip of the syringing pipette is submerged into a fluid sample. The vacuum that forms in the cylinder channel causes at least a portion of the fluid sample to be drawn through the tip opening into the cylinder channel. Such action is referred to herein, when used in reference to a syringing pipette, as "withdraw," "withdrawn," "withdrawal," or any variation thereof. Further, such action can also be referred to herein, when used in reference to a syringing pipette, as "extract," "extracted," "extraction," and any variation thereof. E.g., a sample portion is withdrawn or extracted from a vial using the exemplary syringing pipette.

In contrast, as the piston is moved in a downward direction, the annular seal is pushed downward into the piston channel allowing a positive pressure to develop between the annular seal and any fluid that is present in the cylinder chamber. The positive pressure that develops causes any fluid present in the cylinder channel to become discharged through the tip opening. Such action is referred to herein, when used in reference to a syringing pipette, as "syringe," "syringed," "syringing," and any variation thereof. Further, such action can also be referred to herein, when used in reference to a syringing pipette, as "inject," "injected," "injection," and any variation thereof. E.g., a sample portion is "syringed" or "injected" into a sample container.

Further, the syringing pipette assembly will have an upper annular locking mechanism formed in the piston and a lower annular locking mechanism disposed between a distal end of the piston housing and a collar. The collar and the lower annular locking mechanism will have channel sections allowing the piston channel to open into the cylinder channel. Preferably, the piston housing, the annular locking ring, and the collar are dimensioned such that they allow the syringing pipette to freely move along a transfer track between various positions of the head 252 but become engaged by locking assemblies at the sample extraction station 258 and the sample syringing station 259. In an embodiment of the invention, the head 252 may be designed to be a rotating head wherein each of the pipette holding assemblies are resiliently attached to the rotating head and the entire head assembly rotates from station to station.

A syringing pipette holding assembly 430 generally includes a shell, a locking sleeve, and piston support body. The syringing pipette holding assembly retrieves the syringing pipette at the syringing pipette retrieval station 256. In an embodiment of the invention, the syringing pipette holding assembly 430, will move from the syringing pipette retrieval station 256, then to the sample extraction station 257, then to the sample syringing station 258, and then to the syringing pipette discard station 259. After the used syringing pipette 400 is discarded in the syringing pipette discard station 259, the syringing pipette holding assembly 430 rotatably moves to the syringing pipette retrieval station 256 to begin the sequence again.

In this exemplary embodiment of the syringing pipette assembly, the head 252 with the pipette holding assemblies 430 extend downward in a vertical plane. Preferably, the head 252 with the pipette holding assemblies 430 extends downward in the vertical plane after the pipette holding assemblies have individually become positioned in each of the stations. Without intending to be bound by theory, the purpose of such downward movement can depend upon the function being performed at each of the stations. For example, the syringing pipette holding assembly 430 becomes positioned in closer proximity to the syringing pipette 400 that it is to retrieve from the syringing pipette cartridge 254 at the syringing pipette retrieval station 256; the tip 410 of the syringing pipette 400 pierces and penetrates the sample vial cap 482 allowing sample to be withdrawn and syringed from the sample vial 480, as disclosed herein, at the sample extraction station 257; and the tip 410 of the syringing pipette 400 is positioned in the sample container of the sequential centrifuge allowing the sample portion to preferably be layered therein at the sample injection station 258.

All parts of the syringing pipette holding assembly 430 and syringing pipette 400 become firmly secured in place at the sample extraction station 257. When the rotary head 252 extends downward, the tip of the syringing pipette, which is aligned with a sample vial 480, will pierce the sample vial cap 482 and extend into the sample contained within the sample vial 480. Once the tip is positioned in the sample vial 480, the piston is extended upward causing a portion of the sample to be drawn into the cylinder channel of the syringing pipette 400. Conversely, the piston moves in a downward direction to cause any fluid held within the cylinder channel to exit the syringing pipette 400.

Preferably, a syringing pipette holding assembly 430 and syringing pipette 400 at the sample extraction station 257 will repeat these extraction and syringing operations a multiple number of times. Without intending to be bound by theory, extracting a sample portion from the sample vial and then syringing the sample portion back into the sample vial 480 will cause the sample to become better mixed in the sample vial. Notwithstanding these optional syringing operations, the syringing pipette will finally withdraw at least a portion of the sample at the sample extraction station 257 and proceed to the next station, the sample injection station 258.

At the sample injection station 258, the syringing pipette 400 is aligned with a sample container with its tip proximal to the opening of the sample container that is to be used in the sequential centrifugation module. Preferably, the sample container is already present in a sample reservoir of the sequential centrifuge. A syringing operation, similar to that described herein, is performed at the sample injection station 258. The syringing operation injects at least a portion of the sample withdrawn from the sample vial 480 at the sample extraction station 257 into the sample container. Preferably, when the sample container comprises a density gradient medium, the sample portion is layered into the sample container. The term "layer," "layering," or "layered," as interchangeably used herein with respect to injecting a sample portion into the sample container, means to cause the injected sample to become disposed such that it is substantially contacted with the surface of the density gradient medium.

Once sample injection is complete at the sample injection station 258, the syringing pipette holding assembly 430 and syringing pipette 400 moves to the syringing pipette discard station 259. At the syringing pipette discard station 259, the syringing pipette holding assembly 430 releases the used syringing pipette. Once this operation is complete, the syringing pipette holding assembly 430 is ready to be returned to the syringing pipette retrieval station 456 to begin the sequence again.

In a preferred embodiment of the invention, the head 252 has four syringing pipette holding assemblies 430 that perform the syringing pipette retrieval operation, sample mixing and extraction operations, sample injection operation, and used pipette discarding operation simultaneously. This preferred embodiment of the invention is illustrated in FIG. 7, which is a section view taken along the VII-VII line of FIG. 6. FIG. 8 is a flowchart showing the steps of the syringing pipette assembly being performed simultaneously according to an embodiment of the invention.

In another aspect of the invention, in addition to transferring and preparing a sample for processing in the sequential centrifuge, a sample transfer module may be provided such that at least one of an aliquot, a diliquot, and any combinations thereof can be prepared inline. As used herein, the term "aliquot" means at least a portion of a sample. For example, an aliquot may be dispensed into a labeled vial and held as a backup in the event further preparation and/or analysis is needed.

As used herein, the term "diliquot" means the combination of at least another portion of a sample with at least one other reagent. For example, the diliquot may be prepared by combining at least one other reagent with at least another portion of a sample at least one of prior to, substantially contemporaneously with, and sometime after dispensing the at least another portion of a sample. The prepared diliquot may be routed to another laboratory and/or subjected to further preparation and analysis.

FIG. 9 is a top view of a sample transfer module for the inline preparation of additional aliquot and diliquot samples. In the preferred embodiment where the sample transfer module is a syringing pipette assembly 360, a syringing pipette is retrieved at a syringing pipette retrieval station 362. The retrieved syringing pipette is advanced to a sample extraction station 364 where at least a portion of a sample is drawn into the syringing pipette. Some part of the drawn sample is transferred to a sample container for centrifugation at the sample syringing station 368. Another part of the drawn sample is used to prepare an aliquot at the aliquot preparation station 370. Yet another part of the drawn sample is used to prepare a first diliquot sample at the first diliquot preparation station 372. Even yet another part of the drawn sample is used to prepare a second diliquot sample at the second diliquot preparation station 374. The spent syringing pipette is ejected from the syringing pipette assembly at the syringing pipette discard station 376. As can be envisioned by a person having ordinary skill in the art having the benefit of this disclosure, a sample transfer module can be provided to prepare any number of aliquots and/or diliquots inline.

FIGS. 10A, 10B, 10C, 10D, 10E, 10F, 10G, and 10H are top plan views illustrating various positions of the sample transfer module according to the illustrative embodiment of FIG. 9. A syringing pipette is retrieved at the syringing pipette retrieval station 362 when the syringing pipette assembly 360 advances to its next position. As the syringing pipette assembly 360 advances through various positions, at least a portion of samples 382, 384, 386, 388, 390, and 392 are drawn into their respective syringing pipettes at the sample extraction station 364. Some part of each of drawn samples 382", 384", 386", and 388" are transferred to their respective sample containers for centrifugation at the sample syringing station 368. For example, some part of each of the drawn samples 382", 384", 386", and 388" may be layered over density reagents in their respective sample containers. Another part of each of the drawn samples 382''', 384''', and 386''' are used to prepare an aliquot at the aliquot preparation station 370. For example, a part of the drawn samples 382''', 384''', and 386''' can be dispensed into their respective vials to be stored and then retrieved, if needed, for example, for subsequent analysis. Yet another part of the drawn samples 382' and 384"" are used to prepare first diliquots samples at the first diliquot preparation station 372. The first diliquot sample may be routed to another laboratory and/or subjected to further preparation and analysis. Even yet another part of the drawn sample 382''''' can be used to prepare a second diliquot sample at the second diliquot preparation station 374. The second diliquot sample may be routed to another laboratory and/or subjected to further preparation and analysis. The spent or used syringing pipettes are ejected from the syringing pipette assembly 360 at the syringing pipette discard station 376.

FIG. 11 is a flowchart showing the steps of the syringing pipette assembly being performed simultaneously including preparing at least one aliquot and, according to this exemplary embodiment, preparing two diliquots. Of course, having the benefit of this disclosure, a person of ordinary skill in the art may contemplate other configurations of the syringing pipette system. Such configurations may include, for example, the preparation of at least one aliquot whereby no diliquots are prepared, the preparation of one or more diliquots whereby no aliquots are prepared, and the preparation of one or any number of aliquots and one or any number of diliquots. In other embodiments of the invention, while the syringing pipette module may be configured to prepare any number of aliquots and any number of diliquots, the preparation of any such aliquots and/or any such diliquots may optionally not be performed. Any number of factors may contribute to the reasons for not preparing any such aliquots and/or any such diliquots including, for example, the type of sample being processed; the analysis (or analyses) to be performed on the sample; the availability of materials to prepare an aliquot and/or diliquot; the ability to subsequently handle, process, or analyze any such prepared aliquots and or diliquots; and any combination thereof.

In another embodiment of the invention, the integrated sample preparation system comprises a sample transfer module having a plurality of syringing pipette assemblies that operate substantially simultaneously, as described herein, to dispense at least a portion of a sample into a sample container of the sequential centrifuge.

The sequential centrifuge module comprises a sequential centrifuge. A sequential centrifuge processes discrete samples individually and sequentially. Sequential centrifugation has many advantages over conventional centrifuges that process discrete samples in batches. The sequential centrifuge typically has a plurality of sample reservoirs. Preferably, the sequential centrifuge also has an indexing system for advancing an index from a current available sample reservoir to a next available sample reservoir and a control system interfaced to the drive subsystem for performing a centrifugation sequence.

Discrete samples that must be centrifuged in order to isolate a particular phase on which further analysis is performed typically requires that a set force, as measured by the relative centrifugal force (RCF), be applied, and the set force be applied over a certain amount of time during centrifugation. The cumulative product of RCF and time applied to the sample, or a total FT, allows a certain degree of separation to be achieved. The term "total FT" as used herein means the sum of the integral of applied RCF in the time periods the RCF was applied to a given sample. Total FT is given by the formula:

$$\text{total } FT = \sum_{i=1}^{n} \int_{t_{i-1}}^{t_i} RCF_i \, dt.$$

As represented above, when a sample is subjected to multiple sequences of acceleration, centrifugation, and deceleration, then the total FT is given by a sum of the total FT for each of the sequences.

A sequential centrifuge generally comprises a centrifuge, an indexing system, and a control system. The centrifuge generally comprises a drive subsystem, a rotor coupled to the drive subsystem, and at least one sample holder affixed to the rotor. The sample holder preferably has a plurality of sample reservoirs for holding samples or sample containers containing samples. The indexing system advances an index from a current available sample reservoir to a next available sample reservoir for identifying where the next sample should be placed in the centrifuge based upon a defined loading strategy. The control system is interfaced to the drive subsystem for performing a centrifugation sequence.

The indexing system may be configured, for example, to choose the next available sample reservoir to be a sample reservoir in a position juxtaposed to the prior sample reservoir that has been loaded with a sample. Alternatively, the indexing system may choose the next available sample reservoir as a sample reservoir needed to maintain balance in the centrifuge. The indexing system may use, to its advantage, the configuration of the system in determining how to best load sample containers within the centrifuge. Other loading configurations, as perceived by persons having ordinary skill in the art with the benefit of this disclosure, are intended to be incorporated into this disclosure.

Figure 12A:
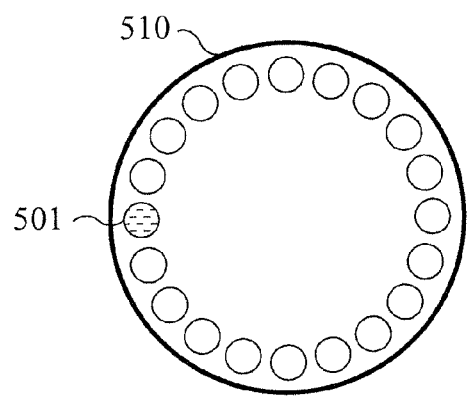
Figure 12B:
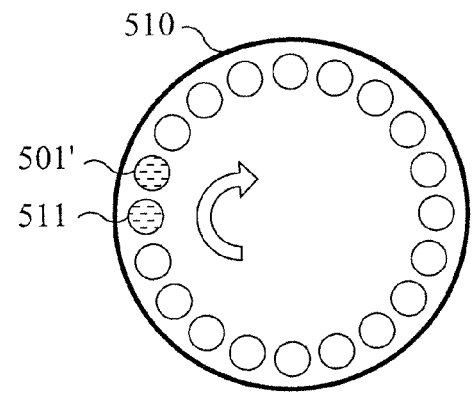
Figure 12C:
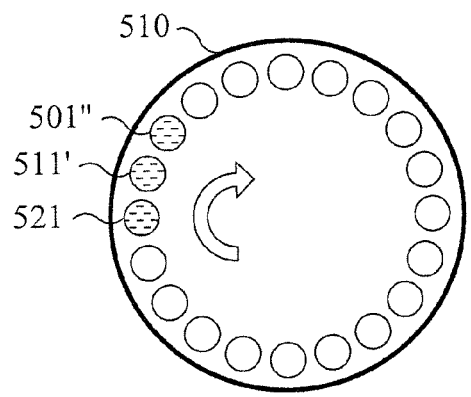
Figure 12D:
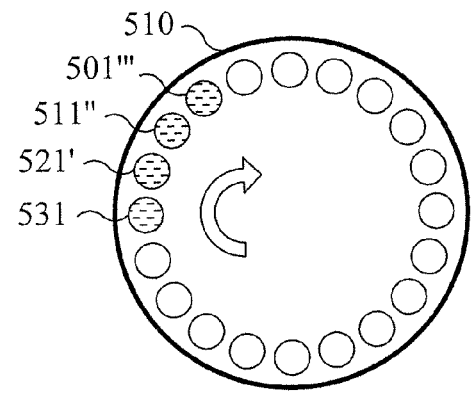

FIG. 12A is a top plan view of a carousel, used in certain embodiments of the invention, showing where a sample is loaded into a first sample reservoir 501 for processing in a first centrifugation sequence. After loading the sample, the centrifugation sequence continues through an acceleration cycle, a centrifugation cycle, and a deceleration cycle. The indexing system advances an index to a next available sample reservoir identifying where the next sample is to be loaded. In this embodiment, the indexing system is configured to advance the index to a next available sample reservoir that is in a position juxtaposed to the current available sample reservoir that has just been loaded with a sample. After coming to a stop, as shown in FIG. 12B, a sample is loaded into a second sample reservoir 511 in a position juxtaposed to the first sample reservoir 501' whose sample remains in the centrifuge for the next centrifugation sequence that includes an acceleration cycle, centrifugation cycle, and a deceleration cycle. As shown in FIG. 12C, when the centrifuge comes to a stop after completing the second cycle, a sample is loaded into a third sample reservoir 521 in a position juxtaposed to the second sample reservoir 511' whose sample remains in the centrifuge along with the sample of the first sample reservoir 501" for a third centrifugation sequence that includes an acceleration cycle, centrifugation cycle, and a deceleration cycle. As shown in FIG. 12D, when the centrifuge comes to a stop after completing another centrifugation sequence, a sample is loaded into a fourth sample reservoir 531 in a position juxtaposed to the third sample reservoir 521' containing a sample remaining in the centrifuge for a second centrifugation sequence. Also remaining in the centrifuge are the sample in the second sample reservoir 511" undergoing a third centrifugation sequence and the sample in the first sample reservoir 501''' undergoing a fourth centrifugation sequence.

Any centrifuged sample that reaches its desired total FT at the conclusion of a centrifugation sequence will be removed from the centrifuge. Of course, the preference for when the sample reservoir that becomes available is used is determined by the indexing system and its corresponding configuration as further disclosed herein.

Figure 13A:
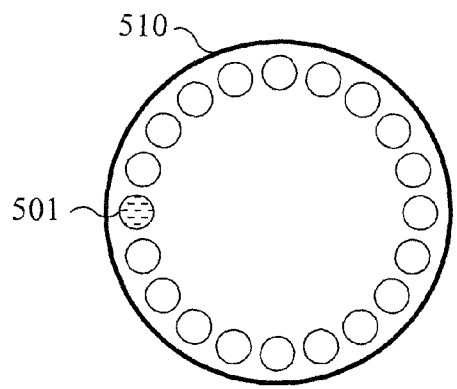
Figure 13B:
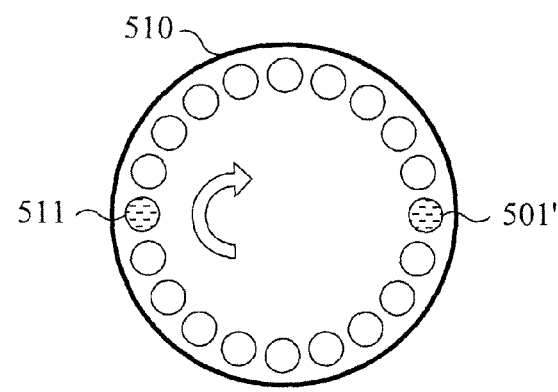
Figure 13C:
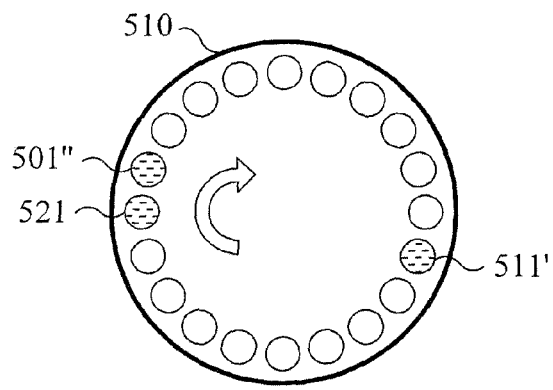
Figure 13D:
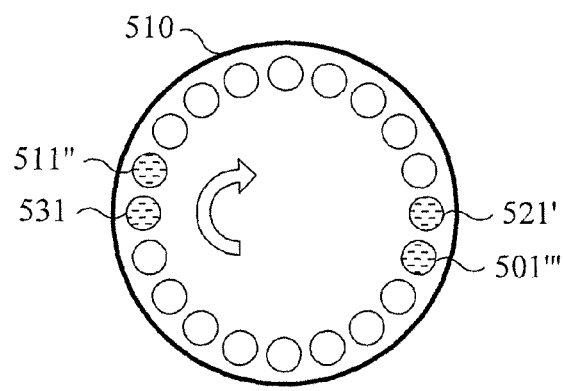

FIG. 13A is a top plan view of a carousel, used in certain embodiments of the invention, showing that a sample is loaded into a first sample reservoir 501 for processing in a first centrifugation sequence. However, in this embodiment, the indexing system is configured to advance the index to a next available sample reservoir that needs to be loaded in order to maintain balance in the centrifuge. FIG. 13B shows that after the centrifuge completes its acceleration cycle, centrifugation cycle, and deceleration cycle, a sample is loaded into a second sample reservoir 511 identified by the indexing system as needed to maintain balance in the centrifuge. FIG. 13C shows that following completion of the next acceleration cycle, centrifugation cycle, and deceleration cycle, a sample is loaded into a third sample reservoir 521 identified by the indexing system as needed to maintain balance in the centrifuge. FIG. 13D shows that following completion of the next acceleration cycle, centrifugation cycle, and deceleration cycle, a sample is loaded into a fourth sample reservoir 531 identified by the indexing system as needed to maintain balance in the centrifuge. The arrangements shown in FIGS. 13A, 13B, 13C, and 13D are merely exemplary of this embodiment. In other embodiments, the indexing system may choose to load samples in a different configuration in order to maintain balance in the centrifuge.

The embodiments in FIGS. 12 and 13 are illustrative of how a single sample is loaded into a sample reservoir at every centrifugation sequence. In the event a sample is not available for loading after the centrifuge has stopped to remove a centrifuged sample that has achieved a desired total FT, the control system can be configured to continue the next centrifugation cycle without sample loading as long as there are samples remaining in the centrifuge that have not reached a desired total FT. Optionally, the control system may be configured to wait a certain period of time before proceeding in the event a sample does become available for loading. Optionally, the sequential centrifuge can also be configured to continue the centrifugation cycle without stopping in the event a sample is not yet available for loading as long as there is no centrifuged sample in the centrifuge that has achieved the desired total FT.

In other embodiments of the invention, the centrifugation sequence can be configured to continue the centrifugation cycle until an event occurs. In one embodiment of the invention, the event includes at least one of a minimum period of time has elapsed, a preset period of time has elapsed, a preset number of samples have become available for loading, and a desired total FT is achieved by any one centrifuged sample. In certain embodiments of the invention, the present number of samples is set to one sample. In other embodiments of the invention, the preset number of samples is set to more than one sample. FIG. 14 is a flowchart of an embodiment of the invention showing the steps of a centrifugation cycle. Of course, if there are currently no available reservoirs in which to load a sample, then the centrifugation cycle can be configured to continue until a desired total FT is achieved by at least one centrifuged sample in order to make a reservoir available for a sample that is available for loading in the next centrifugation sequence (not shown). As used herein, "centrifugation cycle" means the cycle following an acceleration cycle and preceding a deceleration cycle in the centrifugation sequence. The centrifugation cycle can be configured to proceed at a varying RCF. Preferably, the centrifugation cycle will be configured to proceed at a preset RCF that is substantially constant.

FIG. 15 is a flowchart of an embodiment of the invention showing the steps of the centrifugation sequence for processing a critical sample. As the flowchart shows, the critical sample merely needs to be placed in the front at the sample infeed module.

As disclosed herein, in other embodiments of the invention, the sample infeed module partitions samples based on their priority. In the event samples have varying degrees of priority, the samples in the sample infeed module can be arranged in order of descending priority with the highest priority sample being centrifuged first, as earlier disclosed herein. Any sample arrangement method known in the art may be used.

In addition to loading only one sample in each centrifugation sequence, the sequential centrifuge can be configured to load more than one sample or to even load as many samples that are waiting to be loaded subject to available sample reservoirs in the centrifuge. FIG. 16A is a top plan view of a carousel, used in certain embodiments of the invention, showing that a sample is loaded into a first sample reservoir 501 for processing in a first centrifugation sequence. Because, in this example, only one sample is available for loading in this centrifugation sequence, the centrifuge continues to perform an acceleration cycle, a centrifugation cycle, and a deceleration cycle. However, in this example embodiment, while the first sample proceeds through the centrifugation sequence, an additional three samples become available for loading. In this embodiment of the invention, the indexing system is configured to advance the index to a next available reservoir that is in a position juxtaposed to the current available reservoir that has just been loaded with a sample. Therefore, the next three samples now available for loading become loaded into a second sample reservoir 511, a third sample reservoir 512, and a fourth sample reservoir 513 as presented in FIG. 16B. In fact, sample loading and indexing proceed as before with the exception that the other cycles of the centrifugation sequence are not executed until all the samples that are waiting or, optionally, a maximum preset number of samples that are waiting have been loaded up to the limit of available sample reservoirs remaining in the centrifuge. After at least one of all waiting samples have been loaded, the maximum number of samples have been loaded, and no sample reservoirs are available in the centrifuge, the centrifugation sequence proceeds with the acceleration cycle, the centrifugation cycle, and the deceleration cycle. After checking for whether any samples have reached the desired total FT and unloading the same, the system then loads an additional two samples that, in this exemplary embodiment, have become available for loading. The first sample is loaded into the fifth sample reservoir 521 in a position juxtaposed to the fourth sample reservoir 513' and the second sample is loaded into the sixth sample reservoir 522 in a position juxtaposed to the fifth sample reservoir 521 pursuant to the index provided by the indexing system as configured in this embodiment. This loading scheme is shown in FIG. 16C.

As shown in FIG. 16D, when there are no samples waiting to be loaded, the centrifugation sequence can continue the centrifugation cycle without stopping for sample loading as long as there are no centrifuged samples in the centrifuge that have reached the desired total FT. Alternatively, the system may be configured to continue with the deceleration cycle and wait for the next sample that becomes available for loading. In this embodiment of the invention, the time to wait for the next sample may be configured not to exceed a certain period of time.

FIG. 17A is a top plan view of a carousel, used in certain embodiments of the invention, showing where a sample is loaded into a first sample reservoir 501 for processing in a first centrifugation sequence. Because, in this example, only one sample is available for loading in this centrifugation sequence, the centrifuge continues to proceed through an acceleration cycle, a centrifugation cycle, and a deceleration cycle. However, in this example embodiment, while the first sample proceeds through the centrifugation sequence, an additional three samples become available for loading. In this embodiment, the indexing system is configured to advance the index to a next available sample reservoir that needs to be loaded in order to maintain balance in the centrifuge. Therefore, the next three samples now available for loading become loaded into a second sample reservoir 511, a third sample reservoir 512, and a fourth sample reservoir 513 as presented in FIG. 17B. In fact, sample loading and indexing proceed as before with the exception that the other cycles of the centrifugation sequence are not executed until all the samples that are waiting or, optionally, a maximum preset number of samples that are waiting have been loaded up to the limit of remaining available sample reservoirs in the centrifuge. After at least one of all waiting samples have been loaded, the maximum number of samples have been loaded, and no sample reservoirs are available in the centrifuge, the centrifugation sequence proceeds with the acceleration cycle, the centrifugation cycle, and the deceleration cycle. After checking for whether any samples have reached the desired total FT and unloading the same, the system then loads an additional two samples that, in this exemplary embodiment, are waiting to be loaded. The first sample is loaded into the fifth sample reservoir 521 chosen by the indexing system to maintain balance in the centrifuge and the second sample is loaded into the sixth sample reservoir 522 again chosen by the indexing system to maintain balance in the centrifuge. This loading scheme is shown in FIG. 17C.

As shown in FIG. 17D, when there are no samples waiting to be loaded, the centrifugation sequence can continue the centrifugation cycle without stopping for sample loading as long as there are no centrifuged samples in the centrifuge that have reached the desired total FT. Alternatively, the system may be configured to continue with the deceleration cycle and wait for the next sample that becomes available to be loaded. In this embodiment of the invention, the time to wait for the next sample may be configured not to exceed a certain period of time.

The loading arrangements shown in FIGS. 17A, 17B, 17C, and 17D are merely exemplary of this embodiment. In other embodiments, the indexing system may choose to load samples in a different configuration in order to maintain balance in the centrifuge.

In the circumstance when a critical sample becomes available for loading in the embodiments of the invention when multiple samples can be loaded during a centrifugation sequence, the critical sample should be loaded without loading any additional samples unless, perhaps, these additional samples are also identified as critical. FIG. 18 is a flowchart of an embodiment of the invention showing the steps for determining whether there are one or more critical samples that should be processed over other samples waiting to be centrifuged. If one or more critical samples are identified and loaded in the centrifuge, then the acceleration cycle, the centrifugation cycle, and the deceleration cycle can proceed similar to the embodiment disclosed in the flowchart of FIG. 15. According to this embodiment, the centrifuge does not stop for a subsequent sample unless at least one of the subsequent samples is a critical sample, the desired total FT has been achieved for any sample in the centrifuge, and the desired total FT has been achieved for the critical sample in the centrifuge. In other embodiments of the invention, the determination of which critical sample is to be first loaded and whether the centrifuge that is processing a critical sample stops in favor of loading another critical sample that is waiting to be loaded can be determined by a priority ranking of the critical samples.

Having the benefit of this disclosure, a person skilled in the art can contemplate other loading profiles to meet any number of objectives. Such objectives include, but are not limited to, spatial and/or geometric distribution of samples in the centrifuge, some representative embodiments as disclosed herein; organization by sample type; any configuration to maintain balance in the centrifuge, some representative embodiments as disclosed herein; design considerations of the centrifuge and ancillary processing facilities; and any combination thereof. In certain embodiments, the indexing system may index sample reservoirs in other sample holders when the centrifuge comprises a plurality of holders. In yet other embodiments, the indexing system may index sample reservoirs in other sequential centrifuges when more than one sequential centrifuge is in operation. The choice for such a selection may be for any reason as disclosed herein.

Examples of manufacturers whose centrifuges could be used in the invention described herein include, but are not limited to: BD (Becton, Dickinson, and Company) Clay Adams Brand centrifuges (Franklin Lakes, N.J. USA); Beckman Coulter (Fullerton, Calif. USA); Drucker Company (Philipsburg, Pa. USA); and Hamilton Bell Co., Inc. (Montvale, N.J. USA).

The integrated sequential sample preparation system further comprises an extraction module for removing at least a portion of the centrifuged sample from a sample container. In an embodiment of the invention, the extraction module may aspirate a portion of the centrifuged sample from the sample container. In another embodiment of the invention, the extraction system may comprise a plurality of aspirators for removing at least a portion of the centrifuged sample from the sample container after, for example, additional centrifugation sequences or a series of additional centrifugation sequences. For example, after undergoing at least one centrifugation sequence in the sequential centrifuge, a portion of the centrifuged sample may be removed by an extraction module such as an aspirator. In another embodiment of the invention, after undergoing at least one additional centrifugation sequence, a portion of the centrifuged sample may be removed by another extraction module such as another aspirator. In yet other embodiments of the invention, other additional centrifugation sequences and aspiration sequences may be implemented as needed.

In an embodiment of the invention, the extraction module removes a supernatant. In another embodiment of the invention, the extraction module removes a sedimentary layer. Indeed, any layer or combinations thereof may be removed by the extraction module.

In a preferred embodiment of the invention, the extraction module is an aspirator. Generally, an aspirator includes a sample needle. In a preferred embodiment of the invention, the sample needle is removable and can be replaced with another sample needle after extracting a sample portion in order to prevent sample contamination.

Preferably, the aspirator also includes an extension arm assembly capable of being extended downward in order to allow the sample needle to be controllably lowered into a sample container to withdraw a centrifuged sample portion and then to be removed from the sample container once the centrifuged sample portion has been withdrawn. Further, a support post securing the extension arm assembly can rotatably turn allowing the aspirator to pivot about its base. Without intending to be limiting, the ability to rotatably turn the aspirator from one position to another can be useful, for example, to position the sample needle over a sample container so that at least a portion of a sample can be aspirated therefrom and then to position the sample needle over an assay device so that the aspirated portion of the sample can be disposed thereon.

The aspirator may be used to aspirate a sample, dispense a sample, or a combination thereof. In an embodiment of the invention, the aspirator aspirates a sample from a sample container by vacuum suctioning the sample. The vacuum causes a sample to be withdrawn from the sample container through the sample needle. In another embodiment of the invention, the aspirator dispenses a sample that has been withdrawn through a dispensing system by applying a pressure to the sample. The aspirator can be used to first withdraw at least a portion of a sample from a sample container through aspirating the sample. The withdrawn portion of the sample may then be redirected, after the aspirator is repositioned, for example, to an assay device, using the dispensing system.

Preferably, the aspirator will have a control assembly that can be configured to control any movement of the aspirator such as the axial movement of the extension arm assembly and the rotatable movement of the aspirator, the aspiration and dispensing of samples, and the locking and unlocking of the sample needle. The control assembly is useful for aspirating the desired amount of sample from a sample container and dispensing the desired amount of sample as further disclosed herein. Optionally, the aspirator can further include a measuring device for detecting the amount of the sample that is aspirated from a sample container. The signal from the measuring device may be fed to the controller to allow the controller to precisely control the amount of sample that is removed from the sample container.

Nonlimiting examples of commercial aspirators that may be used in an embodiment of the invention include the VABRA™ aspirator manufactured by Berkeley Medevices, Inc. (Berkeley, Calif. USA) or the ADMIRAL™ aspiration systems manufactured by Cole Panner (Vernon Hills, Ill. USA). Any aspirator known in the art may be used in the inventive system.

The centrifuged sample transfer module transfers at least a portion of the centrifuged sample from the sample container onto an assay device. Preferably, the centrifuged sample transfer module comprises an aspiration/dispensing system similar to the device already disclosed herein. In certain embodiments of the invention, in addition to the aspirating and dispensing operations, the aspiration/dispensing device also includes at least one additional line to supply a cleaning solution to the aspirator. In another embodiment of the invention, additional lines supply a cleaning and a rinsing solution to the aspirator. Preferably, in an embodiment of the invention where the device is equipped to only aspirate a sample, contamination is prevented by disposing of the used sample needle. Preferably, in an embodiment of the invention where the device is equipped to aspirate and then dispense a sample, contamination is prevented by disposing of the used sample needle and flushing the aspirator with the cleaning and rinsing solutions. Another representative apparatus for dispensing a sample with subsequent cleaning is disclosed in U.S. Patent Publication No. 2007/0166194 entitled "Automatic Blood Analyzer" to Wakatake, which discloses using a wipeout device and wash water to remove any sample portion remaining on the wall of the sample and dispensing nozzle.

In another embodiment of the invention, the aspirator may use a sample needle that also includes an aliquot channel, with said combination being disposable. The aliquot channel holds the sample that is withdrawn from a sample container. Preferably, aspiration will end before the sample needle becomes completely filled with the sample allowing the aspirator to remain substantially free of any withdrawn sample. The sample contained in the aliquot channel is dispensed by, for example, pressurizing the aspirator and forcing the withdrawn sample from the sample needle. Preferably, the pressurized gas is an inert gas that will not affect the results received from any analysis that is to be performed on the withdrawn sample. The sample needle having an aliquot channel is preferred because it eliminates the need to clean the aspirator after dispensing the sample as otherwise described herein.

In other embodiments of the invention, a centrifuged sample transfer system uses a pipette, such as the syringing pipette, instead of a sample needle for aspirating and dispensing a sample. Preferably, the pipette will be disposable after its use in order to prevent subsequent sample contamination.

Indeed, any system now known or later invented in the art capable of withdrawing a sample and, optionally, dispensing said sample may be used in the inventive system. Examples of such systems include, but are not limited to, those disclosed in U.S. Pat. No. 4,847,205 entitled "Device and Method for Automated Separation of a Sample of Whole Blood into Aliquots" to Burtis et al. (capillary distribution channels); U.S. Pat. No. 5,480,378 entitled "Apparatus for Preparing a Concentrate of Coagulation Factors from a Blood Sample" to Weis-Fogh et al. (device comprising a displacement piston); and U.S. Pat. No. 4,800,164 entitled "Automatic Device for the Analysis and Cloning of Cellular Cultures as Well as for Bacteriological Analysis" to Bisconte (injection device coupled to an aspiration device). A nonlimiting example of a commercial centrifuged sample transfer module that may be used in certain embodiments of the invention include the BD' High Throughput Sampler manufactured by BD (Becton, Dickinson, and Company) (Franklin Lakes, N.J. USA).

Once the centrifuged sample portion has been withdrawn from the sample container, the sample container must then be processed in order to allow the sample reservoir that contains the sample container to process another sample. In an embodiment of the invention, the sample container can be replaced with a clean sample container. A representative example of this embodiment is shown in FIG. 2. A used sample container 292 is removed from the sequential centrifuge 260 by a sample container removal assembly 290, such as a robot arm as already described herein or the motorized loading arm disclosed in U.S. Patent Publication No. 2006/0159587 entitled "Automated Clinical Analyzer with Dual Level Storage and Access" to Fechtner et al. A new sample container is retrieved by a sample container transport mechanism 294 from a sample container cartridge 296. The sample container transport mechanism 294 directs the new sample container to the empty sample reservoir in the sequential centrifuge 260. Finally, the sample container transport mechanism 294 deposits the new sample container in the empty sample reservoir. Optionally, a density gradient medium may be added to a sample container by a density gradient transfer assembly 298. In another embodiment of the invention, the density gradient medium is predisposed in a new sample container that is placed in the sequential centrifuge 260 by the sample container transport mechanism 294. In yet another embodiment of the invention, the sample container remains substantially free of the density gradient medium.

In other embodiments of the invention, the used sample container may be cleaned while it remains in the centrifuge otherwise known as clean-in-place. During a clean-in-place procedure, the used sample container is subjected to a series of washing and rinsing operations. For example, FIG. 19 shows an exemplary clean-in-place procedure using a series of devices to clean the used centrifuge container. A rinsing solution dispensing unit 602 first dispenses a rinsing solution into the used sample container. After being subjected to at least one centrifugation sequence using the sequential centrifuge 260, the contents of the sample container are removed and a cleaning solution is added by a cleaning aspiration/dispensing apparatus 606, for example, similar to the device already described herein. The sample container is again subjected to at least one other centrifugation sequence using the sequential centrifuge 260. The process of aspirating the contents of the sample container, dispensing a cleaning solution, and undergoing at least one centrifugation sequence herein is referred to as a "cleaning sequence." Once the at least one centrifugation sequence is complete, optionally, the sample container may again undergo another cleaning sequence by using either the same cleaning aspiration/dispensing apparatus 606 or another cleaning aspiration/dispensing apparatus (not shown).

After completing any desired number of cleaning sequences, the sample container is then exposed to a rinsing sequence. A "rinsing sequence," as used herein, means the process of aspirating the contents of a sample container and then dispensing a rinsing solution into the sample container using a rinsing aspiration/dispensing apparatus 608, for example, similar to the device already described herein. Finally, the rinsing sequence includes the step of subjecting the sample container to at least one centrifugation sequence using the sequential centrifuge 260. Again, optionally, the sample container may be subjected to any number of rinsing sequences, as needed, either using the same rinsing aspiration/dispensing apparatus 608 or another rinsing aspiration/dispensing apparatus (not shown).

After completing any desired number of rinsing sequences, the sample container is exposed to at least one drying operation using a first dryer 610, but preferably at least one other drying operation after completing at least one centrifugation sequence using the sequential centrifuge 260 using a second dryer 612. The first dryer 610 and, optionally, the second dryer 612 may comprise any drying operation known in the art. Preferably, the drying operation is automated. For example, the drying operation can comprise at least one of blowing gas, preferably a heated gas, into the sample container; wiping the inside walls of the sample container; subjecting the sample container to any of conductive heating, convective heating, radiant heating, and any combination thereof; vacuuming the sample container to remove any contents contained therein; and any combination thereof.

U.S. Pat. No. 4,647,432 entitled "Automatic Analysis Apparatus" to Wakatake discloses another exemplary cleaning means comprising two vacuum pumps each equipped with a vacuum tank for sucking and discharging a cleaning water, a cleaning nozzle, a water supply pump, an electromagnetic valve for disposed in a water pipe for discharging water from the container, and check valves to control the flow of water into and out of the container. However, any cleaning operation that cannot be adapted to operate over the course of several sequential centrifugation sequences is less preferred since it could compromise the speed at which the inventive system can operate.

In another embodiment of the invention, the sample container that has been cleaned in place may optionally be loaded with at least one density gradient medium, if needed, using a density gradient transfer assembly 298.

At least one purpose of the integrated sequential sample preparation system is to prepare an assay device with a desired portion of a sample that is to undergo further analysis. The term "assay device" is used herein to describe an apparatus wherein a sample is disposed such that the sample can undergo further analysis. The centrifuged sample transfer module transfers at least a portion of the centrifuged sample from the sample container onto the assay device. Preferably, the assay device is selected such that the sample disposed thereon may undergo the preferred analysis that is to be performed on the sample.

Generally, an assay device comprises a proximal sample application zone from which a distal analysis apparatus may test the sample. Optionally, the sample application zone can be a spatially distinct reservoir. In an embodiment of the invention, a spatially distinct reservoir contains a reagent capable of binding the sample to the assay device. Optionally, the sample application zone is covered with a plate after disposing the sample within the sample application zone.

Examples of assay devices include, but are not limited to, a cassette, a slide including microslides, a Petri dish, a tube, a bottle, a plate including multi-plate assemblies, a cup, a septum, a pipette, a syringe, a titer including microtiters, a capillary array, a tray, a gel pack, a swab, an applicator, any fibrous media, and any combination thereof. Indeed, an assay device may be any media, device, apparatus, or support that is capable of receiving a sample and allows that sample to undergo further analysis.

In an embodiment of the invention, the assay device is a slide. FIG. 20 is a top view of a slide 620 having a sample 626 dispensed thereon. Preferably, an indicia of reference or other device for identifying the sample 622 is included on the slide 620. The indicia of reference or other device for identifying the sample 622 will correspond to the ID assigned by the accessioning module. Optionally, the slide 620 can have a well 624 for holding the transferred centrifuged sample portion.

In an embodiment of the invention, a sample identification module could be positioned to read the indicia of reference or other device for identifying the sample 622 and instruct the controller for the aspirator to at least one of apply a desired amount of sample, apply the sample in a particular way, and any combination thereof depending upon, for example, the nature of the analysis to be performed on the sample.

In an embodiment of the invention, the slide is defined by a surface and the sample becomes adhered to a portion of the surface. In another embodiment of the invention, the portion of the surface where the sample is to be deposited is pretreated with a material, such as a polycationic coating, to allow the sample to more readily become adhered to the surface. In yet another embodiment of the invention, the portion of the surface of the slide where the sample is to be deposited is slightly roughened, for example to a matte finish, to improve adhesion of the sample to the surface. In even yet other embodiment of the invention, the portion of the surface of the slide where the sample is to be deposited is both slightly roughened and pretreated with a material to improve adhesion of the sample to the surface.

In an embodiment of the invention, a slide processing and a slide transfer module or, collectively, a slide management system, manages the slide. A slide upon which a sample is to be disposed is supplied by a slide cartridge. A slide is withdrawn from the slide cartridge by a slide removal device. For example, the slide removal device can be a flexible roller assembly that contacts the slide through an aperture defined within the slide cartridge. The slide is drawn away from the slide cartridge by the flexible roller assembly onto a conveyor, preferably a stepping conveyor. In an embodiment of the invention, an applicator applies an indicia of reference or other device for identifying the sample. In another embodiment of the invention, the slide will already have an indicia of reference or other device for identifying the sample 622 and a sample identification module will read such indicia or other device and associate that slide with an ID assigned by an accessioning module.

In this exemplary embodiment of the invention, the slide is stepped to the next position on the conveyor where a dispensing device, such as, for example, the aspiration/dispensing device further disclosed herein, disposes the sample onto the surface of the slide. Optionally, as explained herein, a cover may be placed over a portion of the surface of the slide upon where the sample is disposed. In another embodiment of the invention, a cover may be placed over a well that is present on the slide to more permanently affix the centrifuged sample portion to the slide, and prevent, for example, the centrifuge sample portion from becoming exposed to contaminants. Preferably, a cover that is applied to the slide will become adheredly affixed to the slide.

Preferably, the conveyor of the slide transfer module will be of sufficient length to give the sample that has been disposed on the slide sufficient time to become adequately adhered to the slide.

In an embodiment of the invention, the slide is directed to a slide preparation module. For example, though not intending to be limiting, the slide preparation module can be a staining module. The purpose of preparing a sample, in particular a cytological sample, is to extract a desired component from the specimen so that an analysis can be performed. For example, whole blood comprises a variety of immiscible components such as red cells, white cells, platelets, etc. Often the analysis must be preformed on the plasma. Once the desired component is isolated, it must be placed in a form suitable for subsequent analysis. Conventionally, such forms or media include slides, for example deep-well slides, or some other container or vial from which the sample analysis can be performed. Optionally, the extracted portion itself may need to undergo additional processing to render it capable of being analyzed depending, for example, on the type of analysis to be performed. Conventional preprocessing techniques may include staining such as that described in U.S. Pat. No. 6,468,764 entitled "Automated Staining and Decolorization of Biological Material" to Gibbs et al.; the monolayer preparation process for preventing deformations of red blood cells described in U.S. Pat. No. 4,266,505 entitled "Apparatus for the Preparation of Blood Samples for Automated Analysis to Bacus; and the process for the homogeneous distribution of dry particles on a specimen slide in a unilayered, planar distribution described in U.S. Pat. No. 4,868,128 entitled "Process for Dry Dispersal of Particles, and a Device for Carrying Out this Process" to Sommer et al. The inventive system can include these, any other processing system known in the art, and processing systems that are later developed.

In another embodiment of the invention, the slide exits the stepping conveyor and is loaded into a slide racking module.

The integrated sequential sample preparation system of the invention may also comprise an analyzer, analysis system, or analyzer module. The art is with replete with analyzers any of which could be included as part of the integrated sequential sample preparation system of the invention. In other embodiments of the invention, an assay device will be prepared using the inventive system and undergo analysis at a later time.

Another aspect of the invention includes methods of use of an integrated sequential sample preparation system. An embodiment of the invention involves a method for preparing a sample in an integrated sequential sample preparation system comprising the steps of accessioning the sample; identifying the sample; vortexing the sample; loading the sample into a current available sample reservoir; centrifuging the sample in a sequential centrifuge; transferring a phase of the centrifuged sample onto a slide; conveying the slide to a slide racking module; and racking the slide in the slide racking module. In another embodiment of the invention, the method for preparing a sample in an integrated sequential sample preparation system further comprises the step of preparing the slide in a slide preparation module. In yet another embodiment of the invention, the sample that is prepared using the method for preparing a slide in a slide preparation module is a critical sample.

All publications mentioned herein, including patents, patent applications, and journal articles are incorporated herein by reference in their entireties including the references cited therein, which are also incorporated herein by reference. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated by those skilled in the art that changes could be made to the embodiments described herein without departing from the broad inventive concept thereof. Therefore, it is understood that this invention is not limited to the particular embodiments disclosed, but it is intended to cover modifications within the spirit and scope of the present invention as defined by the appended claims.

That which is claimed:

1. A method for preparing samples in an integrated sequential sample preparation system comprising the steps of:
    accessioning the samples;
    identifying the samples;
    vortexing the samples;
    loading each of the samples into a current available sample reservoir;
    centrifuging the samples in a sequential centrifuge by:
        performing centrifugation on a first single sample through a series of interrupted centrifugation sequences;
        introducing a second sample into the sequential centrifuge during an interruption of the centrifugation sequence of the first single sample; and
        performing centrifugation on the second single sample through a series of interrupted centrifugation sequences; and
    transferring a phase of each of the centrifuged samples onto an assay device.

2. The method according to claim 1, wherein the accessioning step comprises the step of assigning a unique identifier to each of the samples.

3. The method according to claim 2, additionally comprising the step of identifying the unique identifier of each of the samples using at least one sample identification module.

4. The method according to claim 1, wherein for at least one sample the loading step comprises the steps of:
    retrieving a syringing pipette;
    drawing the sample from a sample vial into the syringing pipette; and
    discarding the syringing pipette.

5. The method according to claim 4, wherein the loading step additionally comprises the step of syringing at least a portion of the sample into the current available sample reservoir.

6. The method according to claim 4, wherein the loading step additionally comprises the steps of:
    disposing the sample into the sample vial to form a mixed sample;
    drawing the mixed sample from the sample vial into the syringing pipette; and
    syringing at least a portion of the mixed sample into the current available sample reservoir.

7. The method according to claim 6, wherein the disposing step and the drawing step are repeated at least once before the syringing step.

8. The method according to claim 6, further comprising layering at least a portion of the mixed sample onto a density gradient medium.

9. The method according to claim 1, additionally comprising the step of aspirating a supernatant from the centrifuged samples.

10. The method according to claim 9, additionally comprising the step of repeating at least once the centrifuging step and the aspirating step.

11. The method according to claim 1, wherein the transferring step additionally comprises the steps of:
   removing the phase of each of the centrifuged samples; and
   disposing the phase onto an assay device.

12. The method according to claim 1, wherein the centrifuging step continues for an amount of time needed to give only a desired volume of the phase of the centrifuged samples.

13. The method according to claim 1, further comprising providing at least two critical samples, performing centrifugation on a first critical sample, and continuing the centrifuging step until a second critical sample becomes available, a desired cumulative product of relative centrifugal force and time (total FT) has been achieved for the first critical sample in the sequential centrifuge, and the desired total FT has been achieved for any other sample in the sequential centrifuge.

14. The method according to claim 1, further comprising providing at least two critical samples, assigning a level of priority to each of the critical samples, and interrupting the centrifugation of the first critical sample only if the second critical sample has a priority at least the same as or greater than the priority of the first critical sample.

15. The method according to claim 1, further comprising providing a slide as the assay device.

16. The method according to claim 15, additionally comprising the steps of:
   conveying the slide to a slide racking module; and
   racking the slide in the slide racking module.

17. The method according to claim 16, wherein the conveying step comprises the step of advancing the slide until there is adequate adhesion of the phase of the centrifuged sample to a surface of the slide.

18. The method according to claim 16, further comprising the step of preparing the slide using a slide preparation module.

19. The method according to claim 18, further comprising providing a staining platform as the slide preparation module.

* * * * *